(12) United States Patent
Duchaussoy et al.

(10) Patent No.: US 7,919,614 B2
(45) Date of Patent: Apr. 5, 2011

(54) SYNTHETIC POLYSACCHARIDES, PROCESS FOR THEIR PREPARATION AND PHARMACEUTICAL COMPOSITIONS CONTAINING THEM

(75) Inventors: Philippe Duchaussoy, Toulouse (FR); Jean Marc Herbert, Tournefeuille (FR); Guy Jaurand, Morsang-sur-Orge (FR); Maurice Petitou, Paris (FR); Constant Van Boeckel, Oss (NL)

(73) Assignees: Sanofi-Aventis, Paris (FR); Azko Nobel, BM Amhem (NL)

( * ) Notice: Subject to any disclaimer, the term of this patent is extended or adjusted under 35 U.S.C. 154(b) by 404 days.

(21) Appl. No.: 10/677,894

(22) Filed: Oct. 2, 2003

(65) Prior Publication Data
US 2004/0068108 A1 Apr. 8, 2004

Related U.S. Application Data

(63) Continuation of application No. 09/686,373, filed on Oct. 11, 2000, now abandoned, which is a continuation of application No. 09/202,241, filed as application No. PCT/FR97/01048 on Jun. 11, 1997, now abandoned.

(30) Foreign Application Priority Data

Jun. 14, 1996 (FR) ..................... 96 07457

(51) Int. Cl.
*A61K 31/716* (2006.01)
*A61K 31/737* (2006.01)
*C08B 11/02* (2006.01)
*C07H 5/10* (2006.01)
*C07H 15/04* (2006.01)

(52) U.S. Cl. ......... 536/123.12; 514/54; 514/57; 536/84; 536/90; 536/92; 536/99; 536/100; 536/123

(58) Field of Classification Search ................... 514/54; 536/211
See application file for complete search history.

(56) References Cited

U.S. PATENT DOCUMENTS

| 5,378,829 A | | 1/1995 | Petitou et al. ................. 536/118 |
| 5,382,570 A | * | 1/1995 | Petitou et al. ................... 514/53 |
| 5,529,985 A | * | 6/1996 | Petitou et al. ................... 514/53 |
| 5,668,274 A | * | 9/1997 | Petitou et al. ................. 536/124 |

OTHER PUBLICATIONS

Oosta et al. "Multiple Functional Domains of the Heparin Molecule" Proc. Natl. Acad. Sci. USA (1981) vol. 78, No. 2, pp. 829-833.*
Paoletti et al. "Atherosclerosis and thrombosis. Old and ner drugs" Archives of Gerontology and Geriatrics (1995) vol. 20, lines 43-48.*
2006 Chemical Abstracts Catalog, STN database descriptions, p. 52, description of CAS Registry database.*
Dreef-Tromp et al., "Polymer-Supported Solution Synthesis of Heparan Sulphate-Like Oligomers" Bioorganic and Medicinal Chemistry Letters (1997) vol. 7 No. 9, pp. 1175-1180.*

* cited by examiner

*Primary Examiner* — Eric S Olson
(74) *Attorney, Agent, or Firm* — Scully, Scott, Murphy & Presser, P.C.

(57) ABSTRACT

Synthetic polysaccharides are disclosed containing 8-24 monosaccharide units made up of a concatenation of disaccharides consisting of a uronic acid and a hexose, wherein the hydroxyl groups of the polysaccharides are etherified with a $C_{1-6}$ alkyl group or esterified in the form of a sulpho group, each disaccharide being at least monoetherified; and salts thereof, are disclosed.

20 Claims, No Drawings

SYNTHETIC POLYSACCHARIDES, PROCESS FOR THEIR PREPARATION AND PHARMACEUTICAL COMPOSITIONS CONTAINING THEM

The present invention relates to novel synthetic polysaccharides having the pharmacological activities of heparin but exerted selectively.

Heparin belongs to the glycosaminoglycan (GAG) family, which are natural heterogeneous sulphated polysaccharides.

The heparin preparations are mixtures of chains comprising a number of monosaccharide units ranging from 10 to 100 and more. To this heterogeneity of size is added a heterogeneity of structure, at the level of the nature of the constitutive monosaccharides, but likewise at the level of the substituents which they carry (L. Roden in: The Biochemistry of Glycoproteins and Glycosaminoglycans, Ed by Lennarz W. J., Plenum Press, 1980, New York and London, 267-371).

Each natural GAG family in general has a range of pharmacological activities. All are combined in the preparations which can be obtained starting from natural products. Thus, for example, the heparins and the sulphated heparans have an antithrombotic activity which is linked to the simultaneous action on several coagulation factors. They likewise exert an action on a number of growth factors, the most well-known being the basic fibroblast growth factor (bFGF).

This action is manifested by an effect on the proliferation of the smooth muscle cells and on angiogenesis. Heparin additionally exerts effects on autoimmunity, inflammation and the formation of tumour metastases.

Heparin especially catalyses the inhibition of two enzymes which intervene in the blood coagulation cascade, namely factor Xa and factor IIa (or thrombin). The heparin preparations of low molecular weight (LMWH) contain chains formed of 4 to 30 monosaccharides and have the property of acting more selectively on factor Xa than on thrombin.

Certain synthetic oligosaccharides, especially those described in EP 84999, have the property of selectively inhibiting, via antithrombin III, factor Xa without any activity on thrombin.

The U.S. Pat. No. 5,378,829 describes sulphated glycosaminoglycanoid derivatives of the heparin or heparan sulphate type having an activity which is antithrombotic and inhibitory of the proliferation of smooth muscle cells. This document, however, only describes oligosaccharides having at the maximum 7 monosaccharide units.

In the course of previous years, the tendency in the field of GAGS was to investigate especially oligosaccharides of the lowest molecular weight possible, but it has been subsequently observed that several of the above-mentioned biological activities are borne by fragments having at least 8 saccharide units. For example, the inhibitory activity of thrombin would necessitate fragments containing at least between 14 and 20 saccharide units whereas for the activation of bFGF at least 12 saccharide units would be necessary (M. Maccarana et al., J. Biol. Chem., 1993, 268, 23998-23905; J. E. Turnbull et al., J. Biol. Chem., 1992, 267, 10337-10341).

A synthesis of polysaccharides of this size presents great difficulties and, in fact, it has never been carried out.

With the aim of discovering the activity of products of lengthy size, it has been proposed to connect two oligosaccharides of small size by an entity which does not intervene in the biological activity. EP 649854 describes such derivatives having antithrombotic activity. Analogously, WO 95 05182 describes conjugates active on the regulation of bFGF.

These products in fact have a selective activity on the different coagulation factors and inhibitory properties of growth factors expressed by an inhibition of cell proliferation.

It has now been found that fragments of GAGs (glycosaminoglycans) containing 8 or more saccharide units and which can be synthesized relatively simply have biological activities which are not only selective but also quantitatively high.

More particularly, it has been found that it is possible to modulate quantitatively the activity of the said polysaccharides according to the length of the chains and the distribution of the functional substituents.

Thus, for example, it has surprisingly been found that sulphated and alkylated decasaccharides can be potent antithrombotics or selective inhibitors of bFGF according to the arrangement of the alkyl groups and of the sulphate groups in the decasaccharide linkage and that it is likewise possible to obtain selective inhibitors of factor Xa, for example with a tetradecasaccharide or products having an activity of the heparin type, namely an activity as much on factor Xa as on thrombin, for example with a hexadecasaccharide.

More generally, it has been found that by production of disaccharide sequences formed by a uronic acid and by a hexose so as to form polysaccharides of 8 to 24 monosaccharide units whose hydroxyl groups are all substituted by alkyl groups or by sulphate groups, it is possible to modulate with precision the activities of the GAGs type to obtain very active and selective products.

Thus, according to one of its aspects, the present invention relates to a novel synthetic polysaccharide containing from 8 to 24 monosaccharide units formed by a sequence of disaccharides formed from a uronic acid and from a hexose, the said polysaccharide being characterized in that all its hydroxyl groups are etherified with a $(C_1\text{-}C_6)$alkyl group or esterified in the form of a sulpho group, each disaccharide being at least monoetherified; as well as its salts, especially pharmaceutically acceptable salts.

Preferably, the invention relates to a polysaccharide such as defined above, characterized in that all its hydroxyl groups are etherified by a methyl group or esterified in the form of a sulpho group, each disaccharide being at least monoetherified; and to its salts, especially pharmaceutically acceptable salts.

Advantageous products are alkylated, preferably methylated, on the hydroxyls in position 2 and 3 of the uronic acid, the said uronic acid preferably being glucuronic acid or iduronic acid and being trisulphated on the hexose, the said hexose preferably being glucose. Another group of preferred products is formed from polysaccharides which are alkylated, preferably methylated, on the hydroxyls in position 3 of the uronic acid, the said acid preferably being glucuronic acid or iduronic acid and being alkylated, preferably methylated, on the hydroxyl in position 3 of the glucose.

The products of the present invention are thus preferably formed from regular sequences of repeated disaccharides formed in turn of glucuronic acid and of glucose or of iduronic acid and of glucose, represented by the following formula:

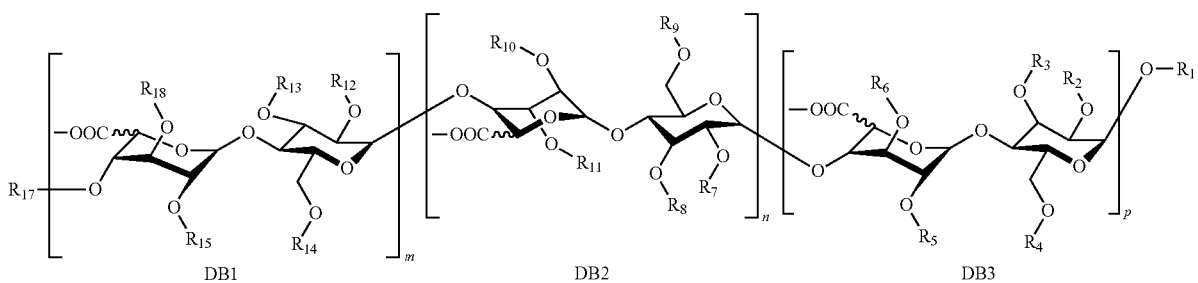

(I)

in which
the wavy line indicates either a bond below or above the plane of the pyranose ring;

$R_1$, $R_6$, $R_{11}$ and $R_{16}$ are a $(C_1\text{-}C_6)$ alkyl;

$R_2$, $R_3$, $R_4$, $R_5$, $R_7$, $R_8$, $R_9$, $R_{10}$, $R_{12}$, $R_{13}$, $R_{14}$, $R_{15}$, and $R_{17}$, are a $(C_1\text{-}C_6)$alkyl or an $SO_3^-$ group;

m, n and p are such that the sum m+n+p is greater than or equal to 4 and less than or equal to 12, one or two of the three being able to be zero, or one of their salts, especially pharmaceutically acceptable salts.

It will be generally noted that in the present invention a wavy line indicates either a bond below or above the plane of the pyranose ring.

In the general formula (I) and in the present description, the structures (a) or (b) below represent a glucose skeleton in the $^4C_1$ conformation. The structures (c) or (d) below represent a uronic acid skeleton which is either of L-iduronic acid (represented here in its $^1C_4$ conformation) or of D-glucuronic acid (represented here in its $^4C_1$ conformation).

On these structures (a), (b), (c) and (d), the $R_x$ substituents have the definitions attributed for $R_1$ to $R_{17}$ in (I).

Thus, the structures (a) and (b) are the same representation of a glucose skeleton in the $^4C_1$ conformation.

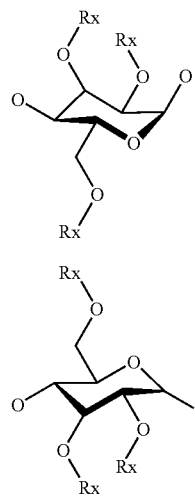

The structures (c) and (d) represent a uronic acid skeleton which is either of L-iduronic acid (represented here in its $^1C_4$ conformation) or of D-glucuronic acid (represented here in its $^4C_1$ conformation).

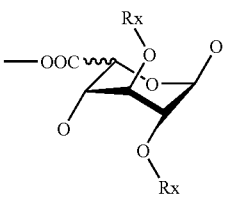

(c)

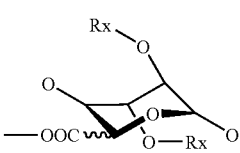

(d)

When the structure is L-iduronic acid (c) and (d) are the following conformers:

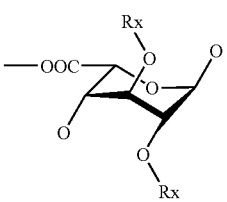 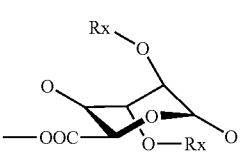

When the structure is D-glucuronic acid (c) and (d) are the following conformers:

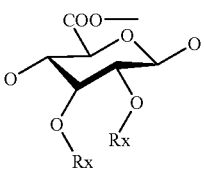 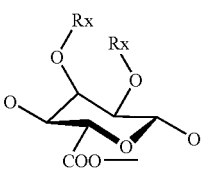

In the present description, it has been chosen to represent the $^1C_4$ conformations for L-iduronic acid, $^4C_1$ conformations for D-glucuronic acid, but it is well known that the conformation in solution of the monosaccharide units is variable.

The disaccharides DB1, DB2 and DB3 represent identical or different disaccharides.

Preferred compounds according to the invention are those of formula (I) in which n and p are equal to zero and m is 4 to and their salts, especially pharmaceutically acceptable salts.

Equally advantageous are the compounds of formula (I) in which n and p are equal to zero, m is 4 to 10; at least one of the substituents $R_{12}$, $R_{13}$, $R_{14}$ and $R_{15}$ is a sulphate group; $R_1$, $R_{16}$ and $R_{17}$ being as defined for (I) as well as their salts, especially pharmaceutically acceptable salts.

Equally advantageous are the compounds of formula (I) in which n and p are equal to zero, m is 4 to 10; at least two of the substituents $R_{12}$, $R_{13}$, $R_{14}$ and $R_{15}$ are a sulphate group; $R_1$, $R_{16}$ and $R_{17}$ being as defined for (I) as well as their salts, especially pharmaceutically acceptable salts.

Equally advantageous are the compounds of formula (I) in which n and p are equal to zero, m is 4 to 10; at least three of the substituents $R_{12}$, $R_{13}$, $R_{14}$ and $R_{15}$ are a sulphate group; $R_1$, $R_{16}$ and $R_{17}$ being as defined for (I), as well as their salts, especially pharmaceutically acceptable salts.

Equally advantageous are the compounds of formula (I) in which n and p are equal to zero, m is 4 to 10; the groups $R_{12}$, $R_{13}$, $R_{14}$ and $R_{15}$ all represent a sulphate group; $R_1$, $R_{16}$ and $R_{17}$ being as defined for (I) and their salts, especially pharmaceutically acceptable salts.

Other advantageous compounds are the salts formed from an anion and from a cation, the anion corresponding to the formula (I.1):

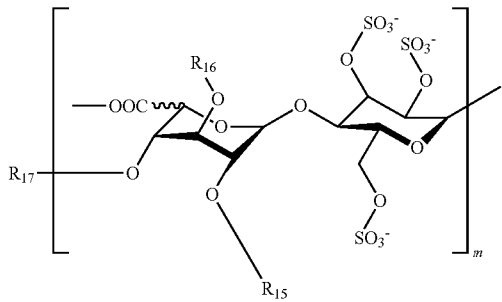

(I.1)

in which m is 4 to 10; $R_1$, $R_{15}$, $R_{16}$ and $R_{17}$ are as defined for (I), each uronic acid being either an iduronic or glucuronic acid, and the cation being a pharmaceutically acceptable monovalent cation, as well as their corresponding acids.

The salts formed from an anion and from a cation where the anion corresponds to the formula (I.2):

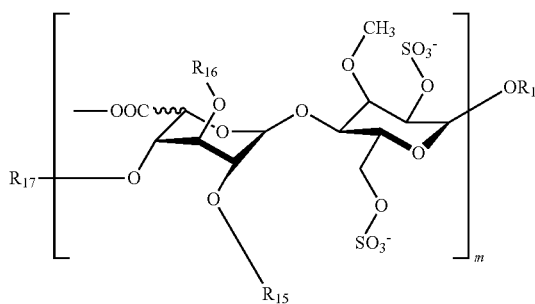

(I.2)

in which m is 4 to 10; $R_1$, $R_{15}$, $R_{16}$ and $R_{17}$ are as defined for (I), each uronic acid being either an iduronic or glucuronic acid and where the cation is a pharmaceutically acceptable monovalent cation, as well as their corresponding acids, are equally advantageous.

In the formulae (I), (I.1), (I.2) above, the etherifying alkyl groups are preferably methyls.

The salts formed from an anion and from a cation, where the anion has the formula (I.3):

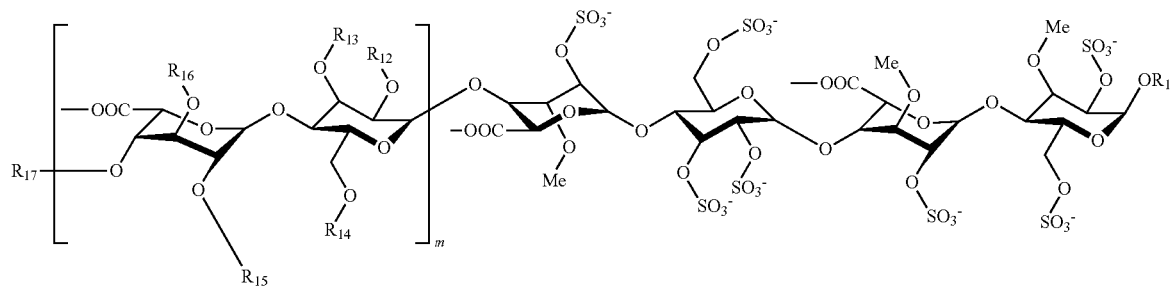

(I.3)

in which m is 2 or 3, $R_1$, $R_{12}$, $R_{13}$, $R_{14}$, $R_{15}$, $R_{16}$ and $R_{17}$ being as defined for (I), each uronic acid being either an iduronic or glucuronic acid and where the cation is a pharmaceutically acceptable monovalent cation, as well as their corresponding acids, are particularly advantageous.

Among these compounds (I.3), those are very particularly preferred for which $R_1$ is a methyl, $R_{13}$ in position 3 of the glucose is a methyl, $R_{12}$ in position 2 and $R_{14}$ in position 6 of the glucose are an $SO_3^-$ and $R_{16}$ in position 3 of the iduronic or glucuronic unit is a methyl, m being equal to 2 or 3.

The preferred salts of the invention are those of which the cation is selected from the cations of the alkali metals and most preferably also those of which the cation is $Na^+$ or $K^+$.

The following polysaccharides are particularly preferred:
1) methyl (1-4)-O-(2,3-di-O-methyl-4-O-sulpho-α-L-idopyranosyluronic acid)-[(1-4)-O-(2,3,6-tri-O-sulpho-α-D-glucopyranosyl)-(1-4)-O-(2,3-di-O-methyl-α-L-idopyranosyluronic acid)]$_9$-2,3,6-tri-O-sulpho-α-D-glucopyranoside, sodium salt,
2) methyl (1-4)-O-(2,3-di-O-methyl-4-O-sulpho-α-L-idopyranosyluronic acid)-[(1-4)-O-(2,3,6-tri-O-sulpho-α-D-glucopyranosyl)-(1-4)-O-(2,3-di-O-methyl-α-L-idopyranosyluronic acid)]$_4$-2,3,6-tri-O-sulpho-α-D-glucopyranoside, sodium salt,
3) methyl (1-4)-O-(2,3-di-O-methyl-4-O-sulpho-α-L-idopyranosyluronic acid)-[(1-4)-O-(2,3,6-tri-O-sulpho-α-D-glucopyranosyl)-(1-4)-O-(2,3-di-O-methyl-α-L-idopyranosyluronic acid)]₅-2,3,6-tri-O-sulpho-α-D-glucopyranoside, sodium salt, 4) methyl (1-4)-O-(2,3-di-O-methyl-4-O-sulpho-α-L-idopyranosyluronic acid)-[(1-4)-O-(2,3,6-tri-O-sulpho-α-D-glucopyranosyl)-(1-4)-O-(2,3-di-O-methyl-α-L-idopyranosyluronic acid)[₆-2,3,6-tri-O-sulpho-α-D-glucopyranoside, sodium salt, 5) methyl (1-4)-O-(2,3-di-O-methyl-4-O-sulpho-α-L-idopyranosyluronic acid)-[(1-4)-O-(2,3,6-tri-O-sulpho-α-D-glucopyranosyl)-(1-4)-O-(2,3-di-O-methyl-α-L-idopyranosyluronic acid)]₇-2,3,6-tri-O-sulpho-α-D-glucopyranoside, sodium salt, 6) methyl (1-4)-O-(2,3-di-O-methyl-4-O-sulpho-α-L-idopyranosyluronic acid)-[(1-4)-O-(2,3,6-tri-O-sulpho-α-D-glucopyranosyl)-(1-4)-O-(2,3-di-O-methyl-α-L-idopyranosyluronic acid)]₈-2,3,6-tri-O-sulpho-α-D-glucopyranoside, sodium salt, 7) methyl (1-4)-O-(2,3-di-O-methyl-4-O-sulpho-β-D-glucopyranosyluronic acid)-[(1-4)-O-(2,3,6-tri-O-sulpho-α-D-glucopyranosyl)-(1-4)-O-(2,3-di-O-methyl-β-D-glucopyranosyluronic acid)]₄-2,3,6-tri-O-sulpho-α-D-glucopyranoside, sodium salt, 8) methyl (1-4)-O-(2,3-di-O-methyl-4-O-sulpho-β-D-glucopyranosyluronic acid)-[(1-4)-O-(2,3,6-tri-O-sulpho-α-D-glucopyranosyl)-(1-4)-O-(2,3-di-O-methyl-β-D-glucopyranosyluronic acid)]₃-2,3,6-tri-O-sulpho-α-D-glucopyranoside, sodium salt, 9) methyl (1-4)-O-(3-O-methyl-2,4-di-O-sulpho-α-L-idopyranosyluronic acid)-[(1-4)-O-(3-O-methyl-2,6-di-O-sulpho-α-D-glucopyranosyl)-(1-4)-O-(3-O-methyl-2-O-sulpho-α-L-idopyranosyluronic acid)]₄-3-O-methyl-2,6-di-O-sulpho-α-D-glucopyranoside, sodium salt, 10) methyl (1-4)-O-(3-O-methyl-2,4-di-O-sulpho-α-L-idopyranosyluronic acid)-[(1-4)-O-(3-O-methyl-2,6-di-O-sulpho-α-D-glucopyranosyl)-(1-4)-O-(3-O-methyl-2-O-sulpho-α-L-idopyranosyluronic acid)]₃-3-O-methyl-2,6-di-O-sulpho-α-D-glucopyranoside, sodium salt, 11) methyl (1-4)-O-(3-O-methyl-2,4-di-O-sulpho-α-L-idopyranosyluronic acid)-[(1-4)-O-(3-O-methyl-2,6-di-O-sulpho-α-D-glucopyranosyl)-(1-4)-O-(3-O-methyl-2-O-sulpho-α-L-idopyranosyluronic acid)]₅-3-O-methyl-2,6-di-O-sulpho-α-D-glucopyranoside, sodium salt, 12) methyl (1-4)-O-(3-O-methyl-2,4-di-O-sulpho-β-D-glucopyranosyluronic acid)-[(1-4)-O-(3-O-methyl-2,6-di-O-sulpho-α-D-glucopyranosyl)-(1-4)-O-(3-O-methyl-2-O-sulpho-β-D-glucopyranosyluronic acid)]₄-3-O-methyl-2,6-di-O-sulpho-α-D-glucopyranoside, sodium salt, 13) methyl (1-4)-O-(3-O-methyl-2,4-di-O-sulpho-α-L-idopyranosyluronic acid)-[(1-4)-O-(3-O-methyl-2,6-di-O-sulpho-α-D-glucopyranosyl)-(1-4)-O-(3-O-methyl-2-O-sulpho-α-L-idopyranosyluronic acid)]α-(1-4)-O-(2,3,6-tri-O-sulpho-α-D-glucopyranosyl)-(1-4)-O-(3-O-methyl-2-O-sulpho-α-L-idopyranosyluronic acid)-3-O-methyl-2,6-di-O-sulpho-α-D-glucopyranoside, sodium salt, 14) methyl (1-4)-O-(3-O-methyl-2,4-di-O-sulpho-α-L-idopyranosyluronic acid)-[(1-4)-O-(3-O-methyl-2,6-di-O-sulpho-α-D-glucopyranosyl)-(1-4)-O-(3-O-methyl-2-O-sulpho-α-L-idopyranosyluronic acid)]α-(1-4)-O-(2,3,6-tri-O-sulpho-α-D-glucopyranosyl)-(1-4)-O-(3-O-methyl-2-O-sulpho-α-L-idopyranosyluronic acid)-3-O-methyl-2,6-di-O-sulpho-α-D-glucopyranoside, sodium salt.

The present invention likewise relates to a process for the preparation of the compounds of formula (I) characterized in that:

(a) a glycosidic link donor monosaccharide is coupled to a glycosidic link acceptor monosaccharide according to the classical methods of sugar chemistry to obtain, after the chemical modifications well known to the person skilled in the art, an intermediate saccharide synthon of completely protected disaccharide type of formula (A):

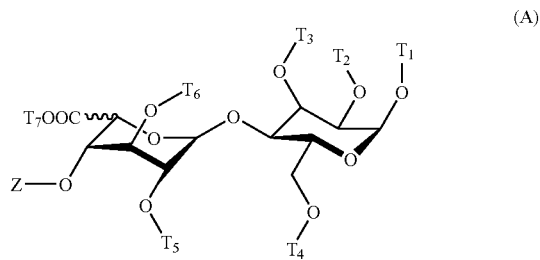

(A)

in which the identical or different $T_1$, $T_2$, $T_3$, $T_4$, $T_5$, $T_6$, $T_7$ and Z substituents are selected from the protective groups used in sugar chemistry as permanent, semi-permanent or temporary protective groups, (b) the disaccharide of formula (A) above is modified chemically so as to obtain an intermediate saccharide synthon of glycosidic link donor disaccharide type of formula (B):

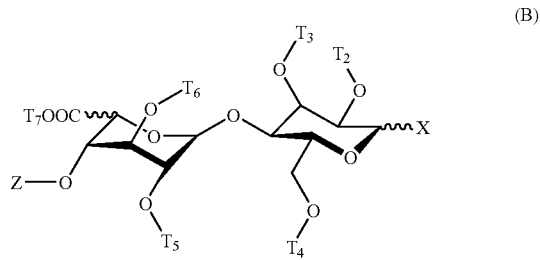

(B)

in which $T_2$ to $T_7$ and Z are such as defined above for (A) and X is an activating group of the anomeric carbon, such as an imidate, a thioglycoside, a pentenylglycoside, a xanthate, a phosphite, a halide or any other group well known for activating the anomeric carbon, then (c) the disaccharide of formula (A) above is modified chemically so as to obtain an intermediate glycosidic link acceptor saccharide synthon of formula (C):

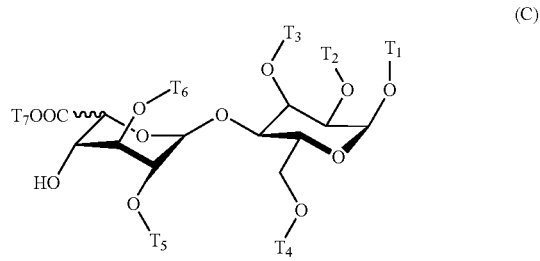

(C)

in which $T_1$ to $T_7$ are such as defined for (A), by selectively eliminating the protective group Z according to methods well known to the person skilled in the art, then (d) a glycosidic link donor disaccharide of formula (B) obtained above and a glycosidic link acceptor disaccharide of formula (C) obtained above are coupled so as to obtain a completely protected tetrasaccharide of formula (D):

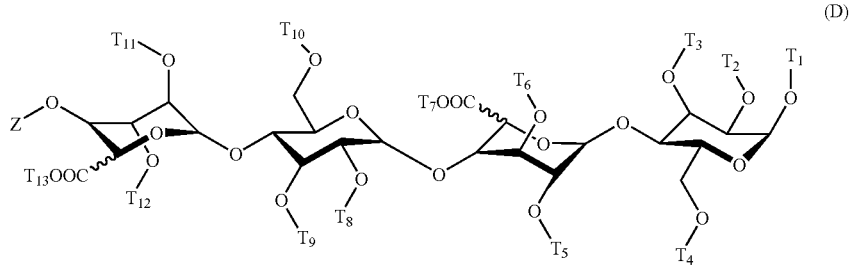

(D)

in which $T_1$ to $T_7$ and Z are such as defined above for (A) and $T_8$, $T_9$, $T_{10}$, $T_{11}$, $T_{12}$ and $T_{13}$ are such as defined for $T_2$ to $T_7$ then, (e) the tetrasaccharide of formula (D) is then modified chemically so as to obtain an intermediate saccharide synthon of glycosidic link donor tetrasaccharide type of formula (E):

in which $T_1$ to $T_{13}$ are such as defined above for (D) then, (g) the glycosidic link acceptor tetrasaccharide of formula (F) and a glycosidic link donor disaccharide of formula (B) such as those obtained above are coupled to form an intermediate saccharide synthon of completely protected hexasaccharide type of formula (G):

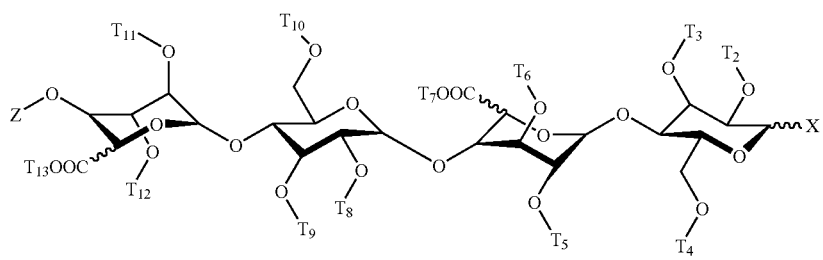

(E)

in which X has the same definition as for (B) and $T_2$ to $T_{13}$ are such as defined for (D) then, (f) the tetrasaccharide of formula (D) is then deprotected selectively so as to obtain a glycosidic link acceptor tetrasaccharide of formula (F):

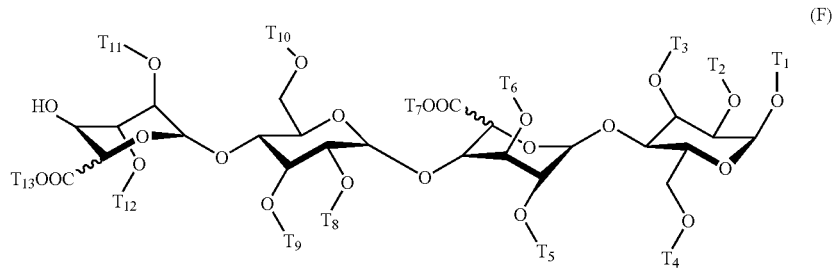

(F)

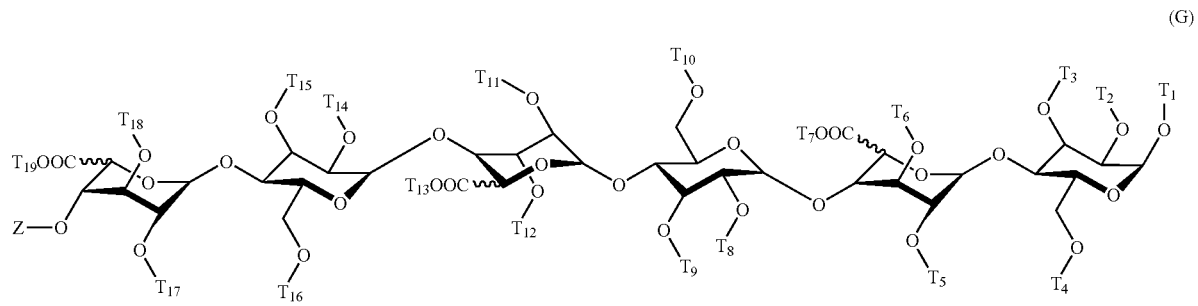

(G)

in which $T_1$ to $T_{13}$ are such as defined above for (D) and $T_{14}$ to $T_{19}$ are such as defined for $T_2$ to $T_7$ for (B), or else the glycosidic link acceptor tetrasaccharide of formula (F) and a glycosidic link donor tetrasaccharide of formula (E) are coupled so as to obtain a completely protected octasaccharide of formula (H):

permanent groups. They are, in addition, groups which are inert with respect to reactions carried out for the introduction of these functional groups and which can be eliminated without these functional groups being altered.

According to the invention, the permanent groups are $C_1$-$C_6$ alkyl groups.

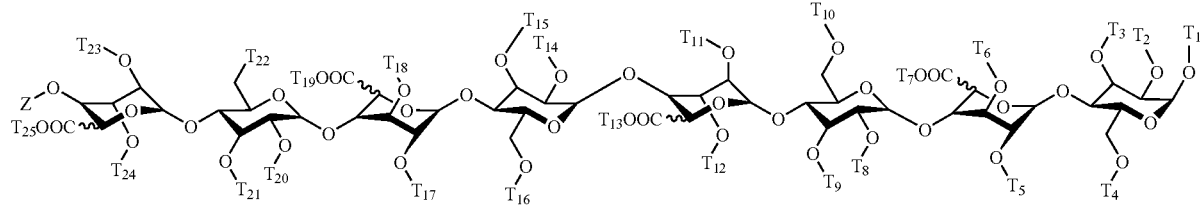

(H)

in which $T_1$ to $T_{19}$ and Z are such as defined previously and $T_{20}$ to $T_{25}$ are such as defined for $T_2$ to $T_7$ for (B) then, (h) the hexasaccharide of formula (G) or the octasaccharide of formula (H) obtained above is modified chemically so as to obtain an intermediate saccharide synthon of glycosidic link acceptor hexasaccharide type of formula (G) in which Z is hydrogen or else a glycosidic link acceptor octasaccharide of formula (H) in which Z is hydrogen, (i) the above deprotection and coupling steps are repeated until the completely protected oligosaccharide having the desired structure is obtained, the glycosyl donor and glycosyl acceptor intermediate saccharide synthons being chosen as a function of the final structure to thus obtain the protected precursor of the desired final polysaccharide of formula (I), in which the nature of the protective groups Ti determines the position of the alkyl and sulphate groups on the final product (I), and (j) the deprotection of the alcohol functions which must be sulphated, and carboxylic acids, is carried out by eliminating the protective groups Ti which protected these functions in the course of the steps of elaboration of the skeleton, then, finally (k) the sulphation is carried out to obtain the compounds (I), or one of their salts.

The process described above is the preferred process of the invention. However, the compounds of formula (I) can be prepared by other methods known from sugar chemistry described, for example, in Monosaccharides, their chemistry and their roles in natural products, P. M. Collins and R. J. Ferrier, J. Wiley & Sons, 1995 and in G. J. Boons, Tetrahedron, 1996, 52, 1095-1121.

As a variant, the compounds of formula (I) can be prepared according to the process described in M. Dreef, XVIIth Carbohydrates Symposium, Ottawa, 1-22 Jul. 1994, Abstract D 2.5.

Semi-permanent groups are understood as meaning groups which can first be eliminated after the glycosylation reactions when the carbohydrate skeleton contains the desired number of units, without removal or alteration of the other groups present, allowing, then, the introduction of desired functional groups into the positions which they occupy.

The permanent groups are groups capable of maintaining the protection of —OH radicals during the introduction of functional groups in place of semi-permanent groups.

These groups are selected from those compatible with the functional groups introduced after elimination of the semi- An example of a semi-permanent and/or temporary group which may be mentioned is benzyl and acetate groups.

The substituents in position 3 of the uronic units of the target compound can be already present in the starting synthons of formula (A), as well as the substituent $R_1$.

In the process above, the substituents $T_1$, $T_6$, $T_{12}$, $T_{18}$ and $T_{24}$ have the same definition as $R_1$, $R_6$, $R_{11}$ and $R_{16}$ in the formula (I), that is to say they are a ($C_1$-$C_6$)alkyl.

The protective groups used in the preparation process of the compounds (I) are those currently used in sugar chemistry, for example, in Protective Groups in Organic Synthesis, T W Greene, John Wiley & Sons, New York, 1981.

The protective groups are advantageously chosen, for example, from amongst the acetyl, halomethyl, benzoyl, levulinyl, benzyl, substituted benzyl, optionally substituted trityl, tetrahydropyranyl, allyl, pentenyl, tert-butyldimethylsilyl (tBDMS) or trimethylsilylethyl ( . . . ) groups.

The activator groups are those classically used in sugar chemistry according to, for example, G. J. Boons, Tetrahedron, 1996, 52, 1095-1121. These activator groups are chosen, for example, from amongst the imidates, the thioglycosides, the pentenylglycosides, the xanthates, the phosphites or the halides.

The process described above allows the compounds of the invention to be obtained in the form of salts. To obtain the corresponding acids, the compounds of the invention in the form of salts are contacted with a cation exchange resin in acid form.

The compounds of the invention in the form of acids can then be neutralized by a base to obtain a desired salt.

For the preparation of the salts of the compounds of formula (I), it is possible to use any inorganic or organic base giving pharmaceutically acceptable salts with the compounds of formula (I).

The base preferentially used is sodium hydroxide, potassium hydroxide, calcium hydroxide or magnesium hydroxide. The sodium and calcium salts of the compounds of formula (I) are the preferred salts.

In step (a) of the process, the protective groups used are those usually used by the person skilled in the art in sugar chemistry, for example according to EP 084999 or alternatively according to Protective Groups in Organic Synthesis, T W Greene, J. Wiley & Sons, 1995.

The protective groups Z, protecting the position 4 of the non-reducing terminal end, and $T_1$, protecting the position 1 of the reducing terminal unit, can be eliminated selectively to allow the functionalization of the corresponding positions of the disaccharide in the course of the following steps of the synthesis. The nature of the other protective groups $T_2$ to $T_8$ is chosen taking account of the alcohol functions which have to be sulphated in the final product. A position carrying an alkyl group in the final product is protected by this group from the start of the synthesis, whereas a position which has to be sulphated is protected by a temporary protective group such as aralkyl (benzyl or substituted benzyl), esters (acetates, benzoates). The position and the nature of the substituents Ti in the final product thus determine the profile of sulphation of the disaccharide fragment originating from (A). It is possible to obtain a great variety of disaccharides of the type of those of formula (A). The preparation of the disaccharides of formula (A) is essentially carried out as described in the Application EP 90201006 or alternatively in the publication C. A. A. van Boeckel and M. Petitou, Angew. Chem. Int. Ed. Engl., 1993, 32, 1671-1690 or alternatively according to G. J. Boons, Tetrahedron, cited above.

According to step (b), it is possible, when $T_1$ is an alkyl, to use an acetolysis reaction in acetic anhydride, which then serves as a solvent and reagent, in the presence of a strong acid such as sulphuric acid or trifluoroacetic acid to liberate selectively the protective group of the anomeric position. When $T_1$ is an ester it is possible selectively to eliminate this ester using, for example, benzylamine and an aprotic solvent such as diethyl ether or dichloromethane, or else alternatively N-methylmorpholine in tetrahydrofuran. When $T_1$ is an allyl group it is possible to isomerize it to vinyl and to then proceed to a mild acid hydrolysis of the vinyl ether, for example in the presence of mercuric chloride in an acetone solution. By means of the methods above, a hydroxylated compound is obtained which is then converted into compound (B), for example by means of a reaction with trichloroacetonitrile in the presence of a base to obtain in this case a compound (B) in which X is an imidate. In the case where X is a thioglycoside, or a pentenylglycoside, the group $T_1$ in the compound (A) can be equal to X.

According to step (c), it is possible to obtain a glycosidic link acceptor disaccharide by selectively eliminating the group Z according to a process well known depending on the nature of Z, employing, for example, (1) hydrazine acetate or hydrazine hydrate, in pyridine or in toluene, in the case where Z is a levulinic group or else (2) thiourea in ethanol in the case where Z is a trichloroacetyl group.

According to step (d), a glycosidic link donor disaccharide of formula (B) obtained above and a glycosidic link acceptor disaccharide of formula (C) obtained above are coupled so as to obtain a completely protected tetrasaccharide of formula (D), for this a known activator of the glycosyl donor X is used, for example trimethylsilyl triflate or TMS or tert-butyldimethylsilyl triflate or TBDMS or alternatively boron trifluoride in diethyl ether, for example when an imidate is involved, or else the N-iodosuccinimide system or NIS, triflic acid when a thioglycoside is involved or any other system known for activating X according to the references cited above. The solvents used for the reaction are preferably dichloromethane, dichloroethane, chloroform, chlorobenzene, diethyl ether, toluene, benzene; the reaction is carried out under anhydrous conditions, and generally at low temperature between −70 and 0° C. It is also possible to carry out the reaction at ambient temperature.

For step (e), the procedure is essentially as described in step (b), starting from the tetrasaccharides obtained according to step (d).

For step (f), the procedure is as described in (c) to selectively deprotect the tetrasaccharides obtained according to step (d), and the tetrasaccharides of formula (F) are obtained.

For step (g), the procedure is as described in step (d), advantageously the products of the reaction of formula (G) are separated by means of gel permeation chromatography.

For step (h), the procedure is essentially as described in step (b), starting from hexasaccharides or from octasaccharides of formula (H) obtained according to step (g).

The above deprotection and coupling steps are repeated until the completely protected oligosaccharide having the desired structure is obtained, the glycosyl donor and glycosyl acceptor intermediate saccharide synthons being chosen as a function of the final structure to thus obtain the protected precursor of the desired final polysaccharide of formula (I), in which the nature of the protective groups Ti determines the position of the sulphate and alkyl groups on the final product (I).

The protective groups of the alcohol functions which must be sulphated are then eliminated according to step (j), by saponification with sodium hydroxide or lithium hydroxide and/or by catalytic hydrogenation, for example in the presence of palladium on carbon.

According to step (k), the sulphation is carried out with the aid of a sulphating agent such as an $SO_3$-amine complex, for example the pyridine-$SO_3$ complex, or with the aid of chlorosulphonic acid in an aprotic solvent such as dimethylformamide, preferably at a temperature of between 0° C. and 100° C., to obtain the compounds (I) which are optionally purified by gel permeation chromatography using water or a solution of sodium chloride as eluent.

The compounds (I) thus obtained can optionally be salified.

The compounds of the formula (I) above likewise comprise those in which one or more hydrogen or carbon atoms have been replaced by their radioactive isotope, for example tritium or carbon 14. Such labelled compounds are useful in research, metabolism or pharmacokinetic work, and in biochemical assays as ligands.

The compounds according to the invention have been the subject of biochemical and pharmacological studies which have shown that they have very interesting properties.

The compounds of the present invention which are bound to AT III ($K_D \leq 200$ nM) or to heparin co-factor (HC II) with an affinity equal to or greater than that of heparin have the anticoagulant properties of heparin.

They therefore inhibit several coagulation factors such as factor Xa (titre≦10μ of anti-Xa/mg) or thrombin ($IC_{50} \leq 10$ μg/ml) and at this titre are excellent antithrombotic agents in models of venous thrombosis and arterial thrombosis.

The affinity of the compounds of formula (I) for AT III has been determined by spectrofluorometry under the conditions described by D. Atha et al. in Biochemistry, 1987, 26, 6454-6461. The results of the assays have demonstrated that the compounds of the invention have a very high affinity for AT III ($K_D$ of between 0.1 μM and 1 nM).

The anti-factor Xa (anti-Xa) activity of the products of the invention has been evaluated at pH 8.4 according to the method described by Teien A. N. and Lie M., in Thrombosis Research, 1977, 10, 399-410, and it has been demonstrated that some compounds of the invention have an anti-Xa activity equal to or greater than that of the synthetic heparinoids already known, and especially is greater than 50μ of anti-Xa/mg.

As has been mentioned above, in the coagulation cascade factor Xa activates prothrombin to thrombin, which proteolyses soluble fibrinogen with liberation of insoluble fibrin, the principal constituent of the blood clot. The inhibition of factor Xa is thus a favoured means of obtaining an anticoagulant and antithrombotic activity.

The global antithrombotic activity of the products of formula (I) has been evaluated by the intravenous route or subcutaneously in the rat, by a model of venous stasis and induction by thromboplastin, according to the method described by J. Reyers et al. in Thrombosis Research, 1980, 18, 669-674. The $ED_{50}$ of the compounds of the invention is at least of the same order or less than that of the other synthetic heparinoids already known ($ED_{50}$ of between 5 and 500 µg/kg). The compounds of the invention thus have a specificity of action and a particularly interesting anticoagulant and antithrombotic activity.

The compounds of the present invention which are capable of modulating, especially of inhibiting, the activity of growth factors, in particular of bFGF, allow the proliferation of vascular smooth muscle cells in culture (CML) to be inhibited with an inhibitory effect which is slightly greater than that of heparin on the growth of the smooth muscle cells.

The action of the compounds of the invention on the activity of bFGF has been evaluated by immobilization of iodinated FGF on human CML in culture.

The inhibition of the proliferation of CML has been evaluated in vitro on cultures of aortic human CML (R. Ross, J. Cell. Biol., 1971, 172-186).

The compounds of the present invention which also have antiviral or hypolipidaemic properties, anti-free radical properties by liberation of superoxide dismutase, or antimetastatic, antiangiogenic or anti-inflammatory properties, can likewise act on the growth and the differentiation of neuronal cells in culture. They are therefore useful in all the pathologies where perturbations of these biological mechanisms intervene.

Some compounds of the invention also exert a protective and regenerative action on the nerve fibres.

Owing to their selective biochemical and pharmaceutical activity, the compounds of the present invention are very interesting medicines. Their toxicity is perfectly compatible with this use. They are also very stable and are thus particularly appropriate for forming the active principle of pharmaceutical specialties.

For their activity on coagulation factors, the compounds of the invention can be used in various pathologies connected with coagulation and in particular in disorders of the cardiovascular and cerebrovascular system. More particularly, they have a great affinity for antithrombin III as well as a significant anti-factor Xa and antithrombin activity. The inhibition of these coagulation factors is thus a favoured means of obtaining an anticoagulant and antithrombotic activity.

They can be used in various pathologies following a modification of the haemostasis of the coagulation system appearing in particular during disorders of the cardiovascular and cerebrovascular system as well as thromboembolic disorders associated with atherosclerosis and with diabetes such as unstable angina, cerebral attack, restenosis after angioplasty, endarterectomy, the fitting of endovascular prostheses; or thromboembolic disorders associated with rethrombosis after thrombolysis, with infarct, with dementia of ischaemic origin, with peripheral arterial diseases, with haemodialysis, with auricular fibrillations or alternatively during the use of vascular prostheses of aorta-coronary by-passes. These products can additionally be used for the treatment or the prevention of thromboembolic pathologies of venous origin such as pulmonary embolisms. They can be used either to prevent or to treat thrombotic complications appearing during surgical interventions or together with other pathologies such as cancer, or bacterial or viral infections. In the case of their use during the fitting of prostheses, the compounds of the present invention can coat prostheses and render them haemocompatible. In particular, they can be attached to intravascular prostheses (stents). In this case, they can optionally be modified chemically by introduction at the non-reducing or reducing end of an appropriate arm, as described according to EP 649 854.

Use in restenosis after angioplasty is favoured by the inhibitory properties of certain growth factors, such as bFGF.

The compounds of the present invention can likewise be used as an adjuvant during endarterectomy carried out with porous balloons.

The results obtained during different pharmacokinetic studies carried out with the products of the invention have demonstrated that they are very well absorbed by the gastrointestinal tract and that their half-life is long. This allows the possibility of a single daily administration to be envisaged during their use in therapeutics.

These studies have also demonstrated that the pharmaceutical compositions prepared with the products of formula (I), the subject of the present invention, are absorbed by the digestive tract without the quantities administered being prohibitive for use in human therapeutics. The compounds of the invention are thus useful for the preparation of pharmaceutical compositions, which can be administered just as easily by the parenteral route as by the oral route.

The compounds of the invention are very stable and are thus particularly appropriate for forming the active principle of medicines.

According to another of its aspects, the present invention relates to a pharmaceutical composition containing, as active principle, a synthetic polysaccharide containing from 8 to 24 monosaccharide units formed by a sequence of disaccharides formed from a uronic acid and from a hexose, the said polysaccharide being characterized in that all its hydroxyl groups are etherified with a $(C_1-C_6)$alkyl group or esterified in the form of the sulpho group, each disaccharide being at least monoetherified; or one of its pharmaceutically acceptable salts. The said synthetic polysaccharide, the active principle of the compositions of the present invention, is preferably alkylated by a methyl group.

The invention preferably relates to pharmaceutical compositions containing, as active principle, a compound of formula (I), (I.1), (I.2), (I.3) or one of its pharmaceutically acceptable salts, optionally in combination with one or more inert and appropriate excipients.

In each dose unit the active principle is present in the quantities adapted to the daily doses envisaged. In general, each dose unit is suitably adjusted according to the dose and the type of administration intended, for example compressed tablets, gelatin capsules and the like, sachets, ampoules, syrups and the like, drops, a transdermal or transmucosal patch so that such a dose unit contains from 0.1 to 100 mg of active principle, preferably 0.5 to 50 mg.

The compounds according to the invention can likewise be used in combination with another active principle useful for the desired therapy such as, for example, antithrombotics, anticoagulants, platelet aggregation inhibitors such as, for example, dipyridamole, aspirin, ticlopidine, clopidogrel or antagonists of the glycoprotein IIb/IIIa complex.

The pharmaceutical compositions are formulated for administration to mammals, including man, for the treatment of the abovementioned illnesses.

The pharmaceutical compositions thus obtained are advantageously presented in various forms, such as, for example, injectable or drinkable solutions, coated tablets, compressed tablets or gelatin capsules. The injectable solutions are the preferred pharmaceutical forms. The pharmaceutical compositions of the present invention are especially useful for the preventive or curative treatment of disorders of the vascular wall, such as atherosclerosis, hypercoagulability states observed, for example, following surgical operations of tumour developments or of coagulation disorders, induced by bacterial, viral or enzymatic activators. The dosage can vary widely as a function of the age, weight and state of health of the patient, of the nature and of the severity of the disorder, as well as of the route of administration. This dosage comprises the administration of one or more doses of approximately 0.1 mg to 100 mg per day, preferably approximately 0.5 to 50 mg per day, by the intramuscular or subcutaneous route, in batchwise administrations or at regular intervals.

The present invention thus likewise relates to the pharmaceutical compositions which contain as active principle one of the above compounds, optionally in combination with another active principle. These compositions are prepared so that they can be administered by the digestive or parenteral route.

In the pharmaceutical compositions of the present invention for oral, sublingual, subcutaneous, intramuscular, intravenous, transdermal, transmucosal, local or rectal administration, the active ingredient can be administered in unitary administration forms, as a mixture with conventional pharmaceutical supports, to animals and to human beings. The appropriate unitary administration forms comprise the forms by the oral route such as compressed tablets, gelatin capsules, powders, granules and oral solutions or suspensions, sublingual and buccal administration forms, subcutaneous, intramuscular, intravenous, intranasal or intraocular administration forms, and rectal administration forms.

When a solid composition in the form of compressed tablets is prepared, the principal active ingredient is mixed with a pharmaceutical vehicle such as gelatin, starch, lactose, magnesium stearate, talc, gum arabic or the like. It is possible to coat the compressed tablets with sucrose or other appropriate materials or alternatively it is possible to treat them in such a way that they have a prolonged or delayed activity and that they liberate a predetermined quantity of active principle in a continuous manner.

A preparation in gelatin capsules is obtained by mixing the active ingredient with a diluent and by pouring the mixture obtained into soft or hard gelatin capsules.

A preparation in syrup or elixir form can contain the active ingredient together with a preferably acaloric sweetener, methylparaben and propylparaben as antiseptic, as well as a taste-imparting agent and an appropriate colourant.

The water-dispersible powders or granules can contain the active ingredient as a mixture with dispersing agents or wetting agents, or suspending agents, such as polyvinylpyrrolidone, as well as with sweeteners or taste corrigents.

For rectal administration, recourse is had to suppositories which are prepared with binders melting at rectal temperature, for example cocoa butter or polyethylene glycols.

For parenteral, intranasal or intraocular administration, aqueous suspensions, isotonic saline solutions or sterile and injectable solutions which contain pharmacologically compatible dispersing agents and/or wetting agents, for example propylene glycol or butylene glycol, are used.

For transmucosal administration, the active principle can be formulated in the presence of a promoter such as a bile salt, a hydrophilic polymer such as, for example, hydroxypropylcellulose, hydroxypropylmethylcellulose, hydroxyethylcellulose, ethylcellulose, carboxymethylcellulose, dextran, polyvinylpyrrolidone, pectins, starches, gelatin, casein, acrylic acids, acrylic esters and their copolymers, vinyl polymers or copolymers, vinyl alcohols, alkoxy polymers, polyethylene oxide polymers, polyethers or a mixture thereof.

The active principle can also be formulated in the form of microcapsules, optionally with one or more supports or additives.

The active principle can also be present in complex form with a cyclodextrin, for example, α-, β- or γ-cyclodextrin, 2-hydroxypropyl-β-cyclodextrin or methyl-β-cyclodextrin.

The active principle can also be liberated by a balloon containing it or by an endovascular extensor introduced into the blood vessels. The pharmacological efficacy of the active principle is thus unaffected.

Administration by the subcutaneous route is the preferred route.

The following METHODS, PREPARATIONS and SCHEMES illustrate the synthesis of the different intermediates useful in obtaining polysaccharides according to the invention.

The EXAMPLES below likewise illustrate the invention without, however, limiting it.

For a better comprehension of the process according to the invention, the obtainment of the compounds (I) can be schematized as follows:

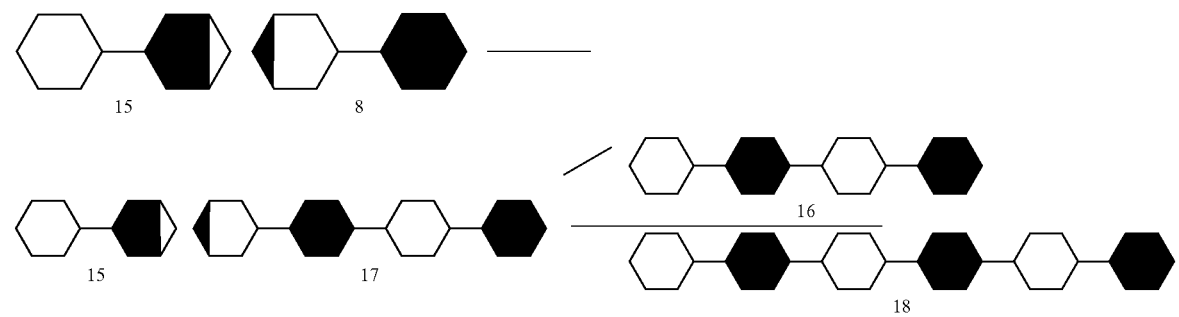

SCHEME 1

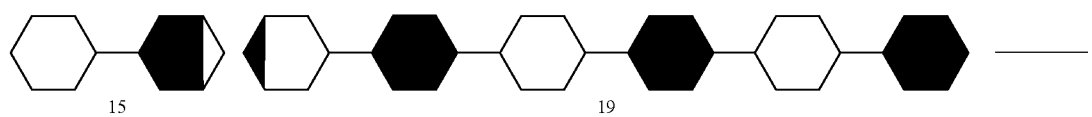
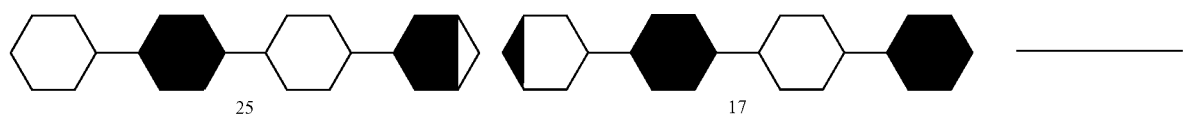
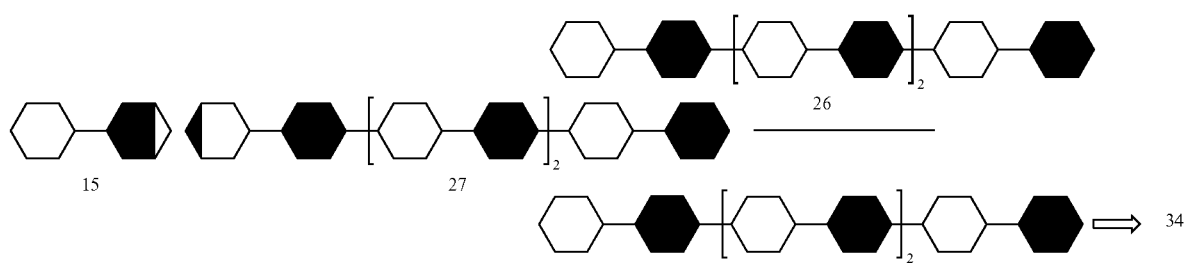
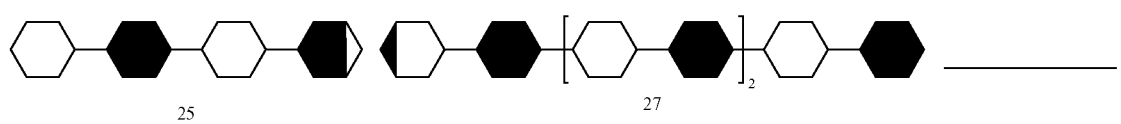
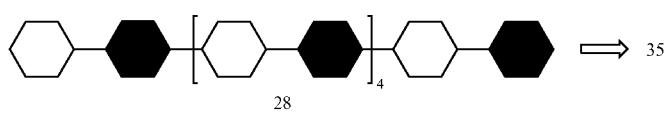
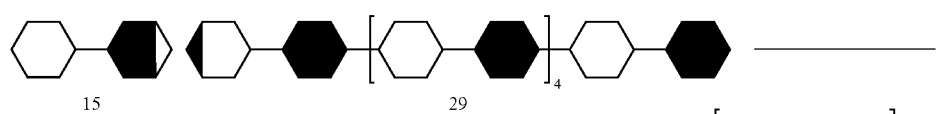
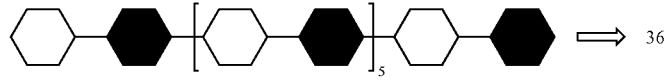
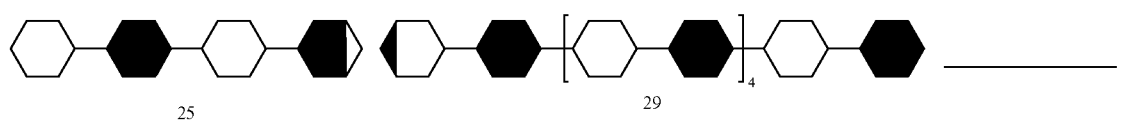
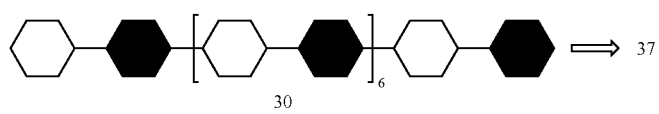

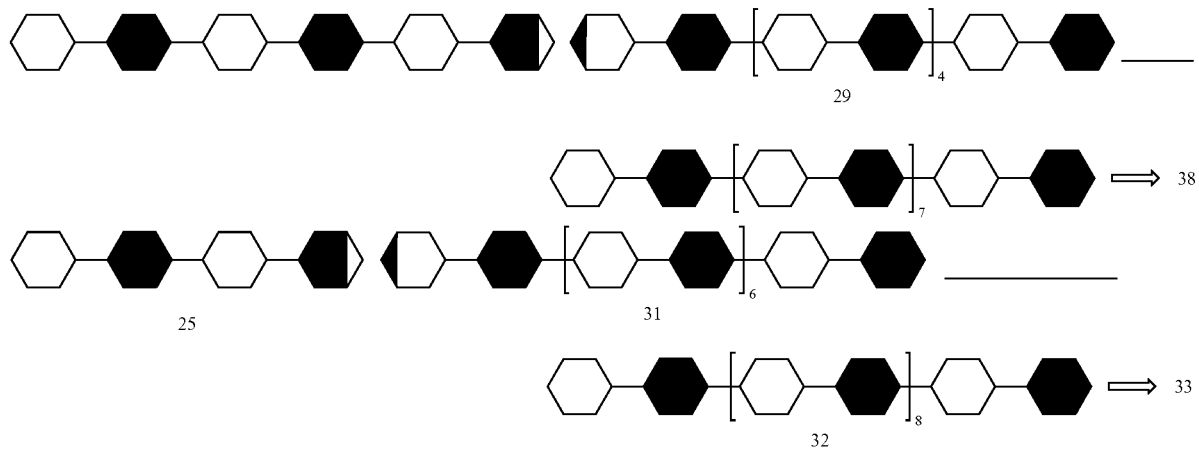

Strategy employed for the synthesis of oligomers of the disaccharide methyl 4-O-(2,3-di-O-methyl-α-L-idopyranosyluronate)-2,3,6-tri-O-sulpho-α-D-glucopyranoside. By condensing the imidates (left column, white triangle at the reducing end) and the glycosyl acceptors (centre column, black triangle at the non-reducing end) completely protected oligosaccharides of the right column are obtained. The latter are then deprotected and functionalized to yield the compounds of EXAMPLE 1 and of TABLE I.

All the compounds described below are homogeneous on thin-layer chromatography (TLC) and have spectral properties in agreement with their structure. The melting points are determined in capillary tubes with the aid of a Mettler apparatus, and are uncorrected. The rotatory powers are measured with the aid of a Perkin-Elmer 241 polarimeter at 22±3° C. The purity of the compounds is checked by TLC on Silica Gel 60® $F_{254}$ (E. Merck) with detection by carbonization in the presence of sulphuric acid. Unless mentioned otherwise, column chromatography was carried out on Silica Gel 60® 40-63 or 63-200 μm (E. Merck). The $^1$H NMR spectra are recorded on Bruker AC 200, AM 250, AC 300 or AM 500 apparatuses, on solutions of the products in $CDCl_3$ or $D_2O$. Before analysis in $D_2O$, the samples are passed through a column of Chelex® ion exchange resin (Bio-Rad) and then lyophilized three times in $D_2O$. The chemical shifts are relative to the external TMS when the spectra are recorded in $CDCl_3$, and to external TSP when the spectra are recorded in $D_2O$. The mass spectrometric analyses are carried out in a ZAB-2E instrument (Fisons). The elemental analyses are carried out in a Fisons analyser.

The following abbreviations are used:
TBDMS: tert-butyldimethylsilyl; Lev: levulinyl; Bn: benzyl; Bz: benzoyl; MCA: chloroacetyl; CCM: thin-layer chromatography; Olm: trichloroacetimidyl; LSIMS: are the initials of Liquid Secondary Ion Mass Spectrometry; ESIMS: are the initials of Electron Spray Ionization Mass Spectrometry; TMS: trimethylsilyl; TSP: sodium trimethylsilyltetradeuteriopropionate; Tf: triflate; MS: molecular sieve.

Dowex®, Sephadex®, Chelex®, Gel 60® are trade marks.

In the METHODS, the PREPARATIONS and in the EXAMPLES described below, general working methods concerning the cleavage of the levulinic esters, the catalytic coupling of the imidates, the deprotection and the sulphation of the oligo- and of the polysaccharides by hydrogenolysis of the esters or of the benzyl ethers, the saponification of the esters or alternatively the sulphations can be carried out by applying the general methods below to the appropriate intermediates.

General Methods

METHOD 1. Cleavage of the Lev Group.

A solution of hydrazine hydrate (1 M in 3:2 pyridine/acetic acid) is added (5 ml/mmol) to a cooled solution (0° C.) in pyridine (5 ml/mmol) of the compound to be treated. After 15-30 minutes (TLC), the solution is concentrated. The residue is dissolved in ethyl acetate, washed with water, a 10% solution of potassium hydrogensulphate, a 2% solution of sodium hydrogencarbonate and with water, and is dried (sodium sulphate) and concentrated.

METHOD 2. Coupling to the Imidates Catalysed by Tert-Butyldimethylsilyl Triflate.

tert-Butyldimethylsilyl triflate (0.5 mol/mol of imidate) is added dropwise, under argon, to a stirred and cooled solution (−20° C.) of the acceptor alcohol and of the donor imidate in toluene (35 ml/mmol), in the presence of 4 Å molecular sieve in powder form. After 15-30 minutes (TLC), solid sodium hydrogencarbonate is introduced with stirring. After 5 minutes, toluene is added, the solution is filtered and washed with a solution of 2% sodium hydrogencarbonate and with water, and is dried (sodium sulphate) and concentrated.

METHOD 3. Coupling to the Imidates Catalysed by Trimethylsilyl Triflate.

Trimethylsilyl triflate (0.04 M in toluene; 0.06 mol/mol of imidate) is added dropwise, under argon, to a stirred and cooled solution (−20° C.) of the acceptor alcohol and of the donor imidate, in toluene (15 ml/mmol), in the presence of 4 Å molecular sieve in powder form. After 15-30 minutes (TLC), solid sodium hydrogencarbonate is introduced with stirring. After 5 minutes, toluene is added, the solution is filtered and washed with a solution of 2% sodium hydrogencarbonate and with water, and is dried (magnesium sulphate) and concentrated.

METHOD 4. Deprotection and Sulphation of the Oligo- and Polysaccharides.

Hydrogenolysis of the benzyl ethers and benzyl esters. A solution of compound (5 mg/ml) in dimethylformamide or methanol is stirred for 2-6 hours (TLC checking) under a hydrogen atmosphere (5 bar) in the presence of 10% Pd/C catalyst (2× mass of the compound). After filtration, the product is employed directly in the following step.

Saponification of the esters. An aqueous solution of 5 M sodium hydroxide is added (in a quantity such that the concentration of sodium hydroxide is 0.5 M at the end of addition) to a solution of an ester in methanol (150 ml/mmol). After 2-5 hours (TLC), water is introduced followed by the resin Dowex® 50 H⁺ to pH 1-2. After filtration and concentration, the residue is passed through a column of Sephadex® G-25 gel (1.6×115 cm) eluted with water. The completely deprotected compound is then obtained after lyophilization.

At this stage, it is checked by ¹H NMR that all the protective groups have been removed. If it is necessary, the product is again subjected to hydrogenation and/or saponification.

Sulphation. Pyridine/sulphur trioxide complex (5 mmol/mmol of hydroxyl function) is added to a solution in dimethylformamide (10 mg/ml) of the compound to be sulphated. After one day at 55° C., the solution is placed on the top of a column of Sephadex G-25 (1.6×115 cm) eluted with 0.2 M sodium chloride. The fractions containing the product are concentrated and desalted by using the same column eluted with water. The final compound is obtained after lyophilization.

SCHEME 2
Synthesis of the disaccharide 5

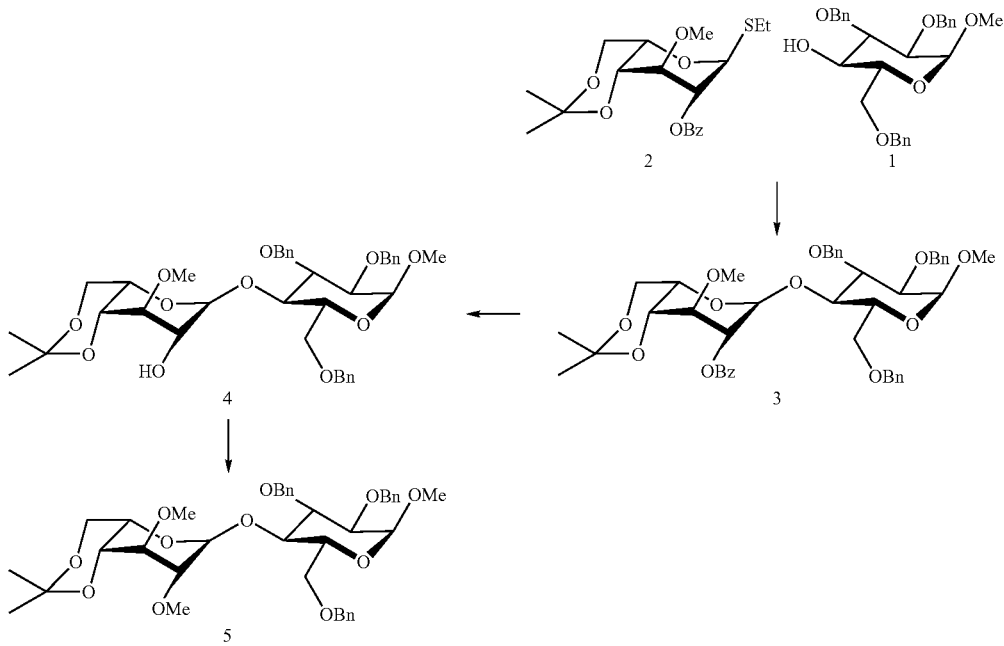

Preparation 1

Methyl 4-O-(2-O-benzoyl-4,6-isopropylidene-3-O-methyl-α-L-idopyranosyl)-2,3,6-tri-O-benzyl-α-D-glucopyranoside (3)

A solution of triflic acid in toluene (0.15 M, 0.27 ml) is added, with stirring under argon, to a cooled solution (-20° C.) of ethyl 2-O-benzoyl-4,6-O-isopropylidene-3-O-methyl-1-thio-α-L-idopyranoside 2 (Jaurand, G. et al., BioMed. Chem. Lett. 1992, 2, 897-900) (1.1 g, 2.87 mmol), of 1 (Garegg P. J., Hultberg H., Carbohydr. Res. 93, 1981 C10-C11) (1.34 g, 2.87 mmol) and of N-iodosuccinimide (1.61 g, 7.2 mmol) in toluene (40 ml) containing 4 Å molecular sieves in powder form. The same quantity of acid is added after 25 and 50 minutes. After 1.5 h, solid sodium bicarbonate (20 mg) is introduced, and, 15 minutes later, the solution is filtered, diluted with dichloromethane, washed with a sodium thiosulphate solution and water, dried (sodium sulphate) and evaporated. The crude product thus obtained (2.49 g) is used directly for the preparation of 4.

After column chromatography (3:1 cyclohexane/ethyl acetate), compound 3 is obtained pure. TLC, $R_F$=0.36, 3:1 cyclohexane/ethyl acetate; $[\alpha]_D$+31 (c=1, dichloromethane) ESI MS, positive mode: m/z+NaCl, 345 (M+Na)⁺; +KF, 361 (M+K)⁺. ¹H NMR (CDCl₃) δ 7.17-7.35 (m, 20H, 4Ph), 5.10 (d, 1H, H-1'), 4.60 (d, 1H, J=3.0 Hz, H-1), 3.37 (s, 3H, OMe), 1.95; 2.04; 2.09 (3s, 9H, 3Ac), 1.24; 1.33 (2s, 6H, :C(CH₃)₂).

Anal. Calculated for $C_{45}H_{52}O_{12}$ (784.86): C, 68.86; H, 6.68. Found: C, 68.61; H, 6.77.

Preparation 2

Methyl 2,3,6-tri-O-benzyl-4-O-(4,6-isopropylidene-3-O-methyl-α-L-idopyranosyl)-α-D-glucopyranoside (4)

A 2 M solution of sodium methoxide (2.2 ml, 4.4 mmol) is added to a solution of compound 3 (2.34 g) in a 1:1 methanol/dichloromethane mixture (13 ml). After 2.5 hours at ambient temperature, the mixture is neutralized with Dowex® 50 resin (H⁺), filtered and concentrated, to give 4 (1.74 g; 86% with respect to 1 and 2) after column chromatography (3:1 then 2:1 cyclohexane/ethyl acetate); $[\alpha]_D$+23 (c=1, dichloromethane). ESI MS, positive mode: m/z+NaCl, 703 (M+Na)⁺; +KF, 719 (M+K)⁺. ¹H NMR (CDCl₃) δ 7.31-7.21 (m, 15H, 3Ph), 4.94 (d, 1H, H-1'), 4.60 (d, 1H, J=3.6 Hz, H-1), 3.44; 3.36 (2s, 6H, OMe); 3.06 (dd, 1H, J=3.6 Hz, J=12.2 Hz, H-6'), 1.31; 1.28 (2s, 6H, :C(CH₃)₂).

Anal. Calculated for $C_{38}H_{48}O_{11}$ (680.76): C, 67.04; H, 7.11. Found: C, 67.05; H, 7.16.

Preparation 3

Methyl 2,3,6-tri-O-benzyl-4-O-(4,6-isopropylidene-2,3-di-O-methyl-α-L-idopyranosyl)-α-D-glucopyranoside (5)

Methyl iodide (3.2 ml, 50.8 mmol) is added, at 0° C., to a solution of 4 (26.6 g, 39.1 mmol) and of sodium hydride (1.48 g, 58.7 mmol) in dimethylformamide (60 ml). A new addition of methyl iodide (1.6 ml, 25.4 mmol) and of sodium hydride (0.74 g, 29.3 mmol) is carried out after 5 hours at ambient temperature. After 1 night, methanol (10 ml) is introduced dropwise, and after 1.5 hours the reaction mixture is concentrated. The product is extracted with ethyl acetate (1.5 l). The solution is washed with water, dried (sodium sulphate) and concentrated. The crude compound 5 thus obtained (32.1 g) is used as such in the following step. TLC, $R_F$=0.55, 3:2 cyclohexane-ethyl acetate.

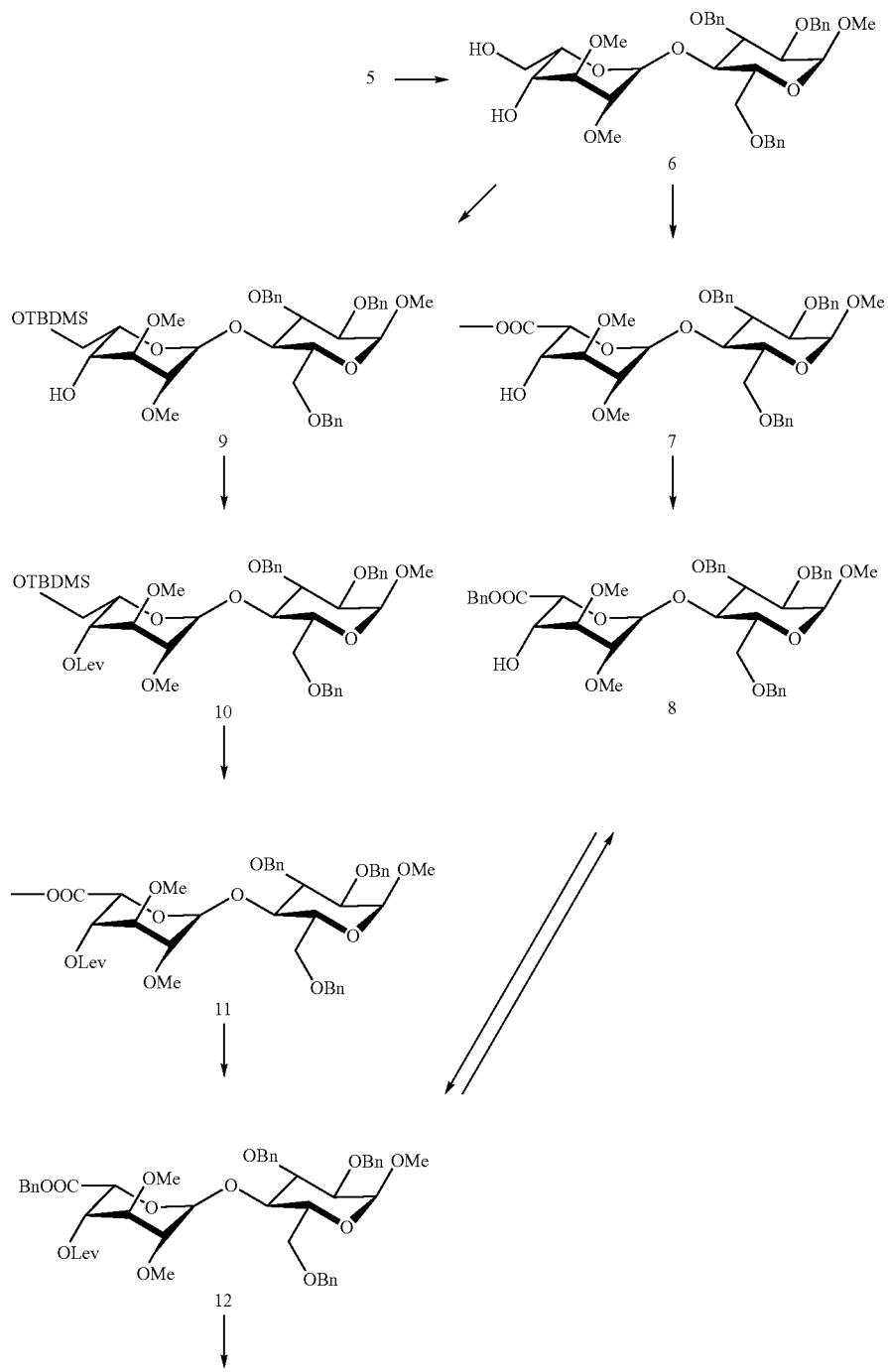

SCHEME 3

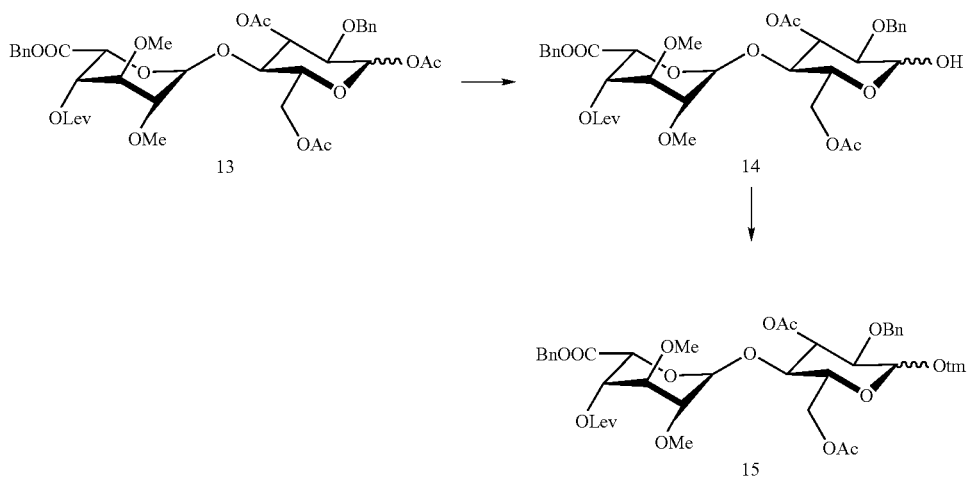

Synthesis of the base disaccharides for the preparation of oligomers of methyl 4-O-(2,3-di-O-methyl-α-L-idopyranosyluronate)-2,3,6-tri-O-sulpho-α-D-glucopyranoside.

Preparation 4

Methyl 2,3,6-tri-O-benzyl-4-O-(2,3-di-O-methyl-α-L-idopyranosyl)-α-D-glucopyranoside (6)

An aqueous solution of trifluoroacetic acid (70%, 43 ml) is added dropwise during the course of 10 minutes to a solution of the above crude compound (32.1 g) in dichloromethane (215 ml). After 25 minutes at ambient temperature, the solution is diluted with dichloromethane (1 l), washed with a saturated aqueous solution of sodium hydrogencarbonate and with water, and dried (sodium sulphate). The crude compound 6 obtained after concentration (27.5 g) is used as such in the following step. TLC, $R_F$=0.29, 2:3 cyclohexane-ethyl acetate.

Preparation 5

Methyl 2,3,6-tri-O-benzyl-4-O-(6-O-tert-butyldimethylsilyl-4-O-levulinyl-2,3-di-O-methyl-α-L-idopyranosyl)-α-D-glucopyranoside (10)

A solution of 6 (1.7 g), of triethylamine (0.54 ml, 3.8 mmol), of 4-dimethylaminopyridine (38 mg, 0.3 mmol) and of tert-butyldimethylsilyl chloride (0.54 g, 3.6 mmol), in methylene chloride (6 ml) is heated at 50° C. for 3 hours to give 9 which is not isolated. After cooling to ambient temperature, levulinic anhydride (0.771 g, 3.6 mmol), triethylamine (0.50 ml, 3.6 mmol) and 4-dimethylaminopyridine (59 mg, 0.48 mmol) are added. After 4 hours, the mixture is diluted with methylene chloride, and washed successively with an aqueous solution of potassium hydrogensulphate, water, a saturated aqueous solution of sodium hydrogencarbonate and water, dried (sodium sulphate) and concentrated to give 10 (2.45 g) which is used as such in the following step. TLC, $R_F$ 0.5, 12:1 cyclohexane/ethyl acetate.

Preparation 6

Methyl 2,3,6-tri-O-benzyl-4-O-(benzyl 4-O-levulinyl-2,3-di-O-methyl-α-L-idopyranosyluronate)-α-D-glucopyranoside (12)

A solution of chromium trioxide (0.64 g, 6.4 mmol) in aqueous sulphuric acid (3.5 M, 2.7 ml) is added slowly to a cooled solution (0° C.) of 10 (2.45 g) in acetone (18 ml). After 5 hours, methylene chloride is introduced, then the mixture is poured into ice water, stirred vigorously, and washed with water to neutral pH and dried (sodium sulphate). Concentration gives (2.45 g) in syrup form. TLC, $R_F$ 0.56, 12:1 methylene chloride/methanol. This product is then dissolved in dimethylformamide (19 ml) and treated for one night at ambient temperature with benzyl bromide (2.9 ml, 12 mmol). Methanol (1.5 ml) is added and the product is extracted with ether, washed with water, dried and concentrated. After column chromatography (2:1 then 3:2 cyclohexane/ethyl acetate) 12 is obtained (1.07 g). TLC, $R_F$ 0.53, 5:1 methylene chloride/ethyl acetate.

Preparation 7

Methyl 2,3,6-tri-O-benzyl-4-O-(benzyl 2,3-di-O-methyl-α-L-idopyranosyluronate)-α-D-glucopyranoside (8)

The disaccharide 12 (0.65 g, 0.76 mmol) treated according to general method 1 gives 8 (0.52 g, 91%) after column chromatography (2:1 then 3:1 cyclohexane/ethyl acetate). $[\alpha]_D$+34 (c=0.97, methylene chloride).

Preparation 8

1,3,6-tri-O-Acetyl-2-O-benzyl-4-O-(benzyl 4-O-levulinyl-2,3-di-O-methyl-α-L-idopyranosyluronate)-D-glucopyranose (13)

Trifluoroacetic acid (28 ml, 0.364 mol) is added to a solution of 12 (7.8 g, 9.1 mmol) in acetic anhydride (194 ml, 2.06 mol) and acetic acid (7.8 ml, 0.136 mol). After heating to 60° C. for 4 hours, the solution is cooled to 0° C. and water (30 ml) is introduced dropwise, followed by triethylamine (69 ml).

After evaporation, the residue is dissolved in dichloromethane, washed with a saturated solution of sodium hydrogencarbonate and water, dried (sodium sulphate) and concentrated. Column chromatography (5:1 dichloromethane/ethyl acetate) gives a mixture (α/β=8/2) of the anomers of 13 (4.7 g, 67%). TLC, $R_F$ 0.35; 3:2 cyclohexane-acetone. $^1$H NMR (CDCl$_3$) δ 7.37-7.20 (m, 10H, 2Ph), 6.30 (d, J=3.6 Hz, H-1α), 5.62 (d, J=7.6 Hz, H-1β), 5.04 (t, 1H, H-4'), 3.45; 3.41 (2s, 6H, 2OMe), 2.6-2.3 (m, 4H, O(C:O)CH$_2$CH$_2$(C:O)CH$_3$), 2.15; 2.12; 2.06; 1.94; 1.88 (5s, 12H, 3 Ac and O(C:O)CH$_2$CH$_2$(C:O)CH$_3$).

Preparation 9

3,6-di-O-Acetyl-2-O-benzyl-4-O-(benzyl 4-O-levulinyl-2,3-di-O-methyl-α-L-idopyranosyluronate)-D-glucopyranose (14)

A solution of ethanolamine (1.3 ml, 21.6 mmol) and of 13 (4.25 g, 5.28 mmol) in tetrahydrofuran (80 ml) is left for one night at 4° C. Ethanolamine (0.65 ml, 10.8 mmol) is then added, then the mixture is left at ambient temperature for 3 h. After cooling to 0° C., 1 M hydrochloric acid is added to acid pH, then dichloromethane (150 ml). The solution is washed with water, dried and concentrated. Column chromatography (2:1 then 1:1 dichloromethane/ethyl acetate) gives 14 (3 g, 74%). TLC, $R_F$ 0.21, 1:1 toluene/ethyl acetate. [α$_D$]+3 (c=1, dichloromethane). LSIMS, positive mode: m/z thioglycerol+NaCl, 769 (M+Na)$^+$; thioglycerol+KF, 785 (M+K)$^+$. $^1$H NMR (CDCl$_3$) δ 7.36-7.25 (m, 10H, 2Ph), 5.21 (d, J=3.5 Hz, H-1α), 4.98 (d, 1H, J=3.4 Hz, H-1'), 4.79 (d, J=8 Hz, H-1β), 3.45; 3.42 (2s, 6H, 2 OMe), 2.56-2.23 (m, 4H, O(C:O)CH$_2$CH$_2$(C:O)CH$_3$), 2.23; 2.12; 1.94; 1.88 (4s, 9H, 2 Ac, α and β O(C:O)CH$_2$CH$_2$(C:O)CH$_3$).

Anal. Calculated for C$_{37}$H$_{46}$O$_{16}$ (746.72); C, 59.51; H, 6.21. Found: C, 58.87; H, 6.13.

Preparation 10

3,6-di-O-Acetyl-2-O-benzyl-4-O-(benzyl 4-O-levulinyl-2,3-di-O-methyl-α-L-idopyranosyluronate)-D-glucopyranose trichloroacetimidate (15)

A mixture of trichloroacetonitrile (0.7 ml, 6.92 mmol), of 14 (1.03 g; 1.38 mmol) and of potassium carbonate (191 mg; 2.21 mmol) in methylene chloride (26 ml) is stirred for 1.5 hours at ambient temperature. The solution is then filtered and concentrated. Column chromatography (4:1 toluene/acetone) gives 15 (1.16 g; 94%). TLC, $R_F$ 0.31 and 0.48, 2:3 cyclohexane/ethyl acetate. LSIMS, positive mode: m/z thioglycerol+LiCl, 896 (M+Li)$^+$; thioglycerol+NaCl, 912 (M+Na)$^+$; thioglycerol+KF, 928 (M+K)$^+$. $^1$H NMR (CDCl$_3$) δ 8.67 (s, NH-β), 8.60 (s, NH-α), 7.37-7.22 (m, 10H, 2Ph); 6.44 (d, J=3.6 Hz, H-1α), 5.83 (d, J=7.3 Hz, H-1β), 3.47; 3.44; 3.42; 3.40 (4s, 6H, 2OMe), 2.7-2.2 (m, 4H, O(C:O)CH$_2$CH$_2$(C:O)CH$_3$), 2.15; 2.08; 1.94; 1.88 (4s, 9H, α and β Ac, and O(C:O)CH$_2$CH$_2$(C:O)CH$_3$).

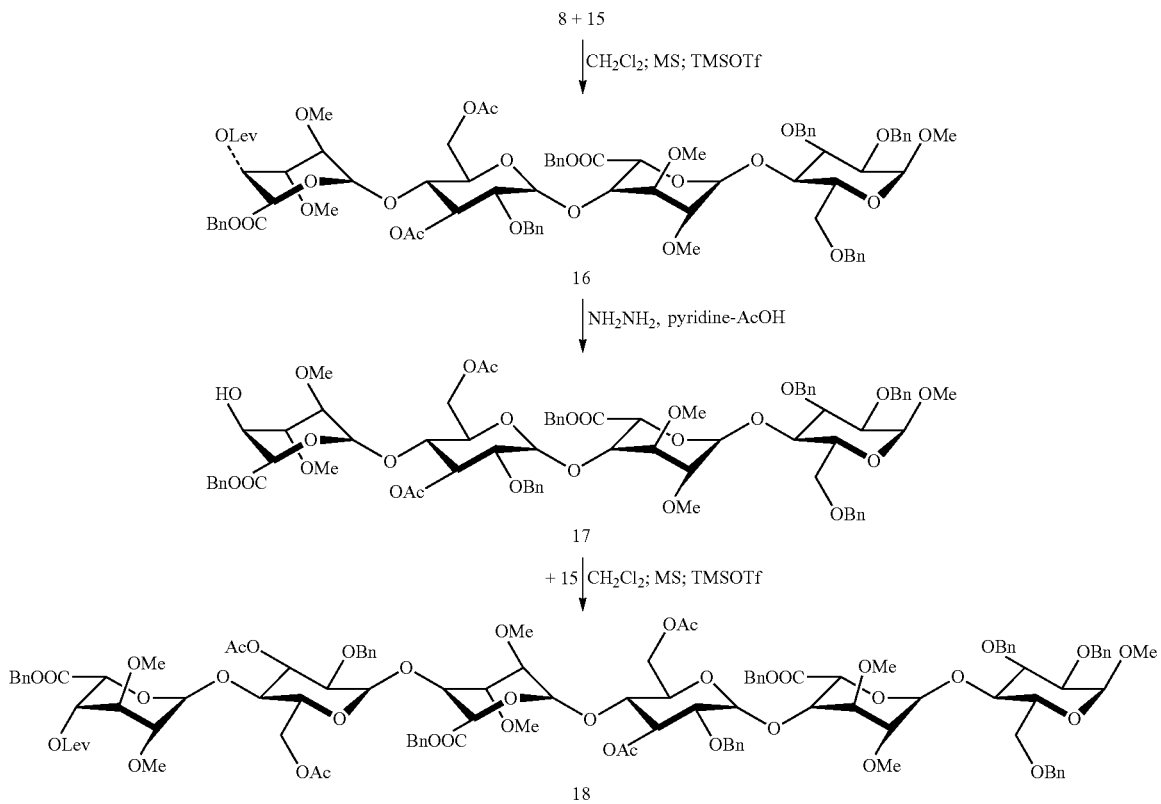

Synthesis of the hexasaccharide 18. The preparation of oligomers of larger size is carried out according to the same strategy (cleavage of the Lev group to obtain a glycosyl acceptor, coupling with a di-, tetra- or hexasaccharide imidate—as indicated in Scheme 1—and finally deprotection and sulphation). The Lev group of 18 is selectively eliminated to give the acceptor hexasaccharide 19 (SCHEME 1).

Preparation 11

Methyl (1-4)-O-(benzyl 4-O-levulinyl-2,3-di-O-methyl-α-L-idopyranosyluronate)-(1-4)-O-(3,6-di-O-acetyl-2-O-benzyl-α-D-glucopyranosyl)-(1-4)-O-(benzyl 2,3-di-O-methyl-α-L-idopyranosyluronate)-2,3,6-tri-O-benzyl-α-D-glucopyranoside (16)

A mixture of 8 (2.90 g, 3.83 mmol) and 15 (4.16 g, 4.67 mmol) is treated according to method 2. Column chromatography (1:1 cyclohexane/ethyl acetate) gives pure 16 (3.2 g; 54%). TLC, $R_F$ 0.52, 2:3 cyclohexane/ethyl acetate. $^1$H NMR (CDCl$_3$) δ 7.21-7.36 (m, 30H, 6Ph), 5.27 (d, 1H, H-1, non-reducing unit), 5.14 (d, 1H, H-1 "central next to non-reducing" unit), 4.90 (d, 1H, H-1, "central next to reducing" unit), 4.56 (d, 1H, H-1 reducing unit), 3.43; 3.39; 3.35; 3.25 (5s, 15H, 5OMe), 2.25-2.60 (m, 4H, O(C:O)CH$_2$CH$_2$(C:O)CH$_3$), 2.12; 2.00; 1.91 (3s, 9H, 2Ac and O(C:O)CH$_2$CH$_2$ (C:O) CH$_3$).

Preparation 12

Methyl (1-4)-O-(benzyl 2,3-di-O-methyl-α-L-idopyranosyluronate)-(1-4)-O-(3,6-di-O-acetyl-2-O-benzyl-α-D-glucopyranosyl)-(1-4)-O-(benzyl 2,3-di-O-methyl-α-L-idopyranosyluronate)-2,3,6-tri-O-benzyl-α-D-glucopyranoside (17)

Compound 16 (1 g; 0.672 mmol) is treated according to method 1 to give 17 quantitatively after column chromatography (1:1 cyclohexane/acetone).

Preparation 13

Methyl (1-4)-O-(benzyl 4-O-levulinyl-2,3-di-O-methyl-α-L-idopyranosyluronate)-[(1-4)-O-(3,6-di-O-acetyl-2-O-benzyl-α-D-glucopyranosyl)-(1-4)-O-(L-benzyl 2,3-di-O-methyl-α-idopyranosyluronate)]$_2$-2,3,6-tri-O-benzyl-α-D-glucopyranoside (18)

A mixture of 15 (386 mg, 434 μmol) and 17 (500 mg; 360 μmol) is treated according to method 2. Column chromatography (Sephadex® LH 20, 195×3.7 cm; 1:1 dichloromethane/ethanol) gives the hexasaccharide 18 (495 mg; 64%). TLC, $R_F$ 0.36; 10:1 dichloromethane/acetone.
$^1$H NMR (CDCl$_3$) δ: 5.23; 5.12; 5.10; 4.92; 4.89; 4.56 ppm.

Preparation 14

Methyl (1-4)-O-(benzyl 2,3-di-O-methyl-α-L-idopyranosyluronate)-[(1-4)-O-(3,6-di-O-acetyl-2-O-benzyl-α-D-glucopyranosyl)-(1-4)-O-(benzyl 2,3-di-O-methyl-α-L-idopyranosyluronate)]$_2$-2,3,6-tri-O-benzyl-α-D-glucopyranoside (19)

Compound 18 (485 mg; 229 μmol) is treated according to method 1. Column chromatography (10:1 dichloromethane/acetone) gives 19 (392 mg; 85%). TLC, $R_F$ 0.38, 10:1 dichloromethane/acetone.

SCHEME 5
Synthesis of the acceptor disaccharide 22

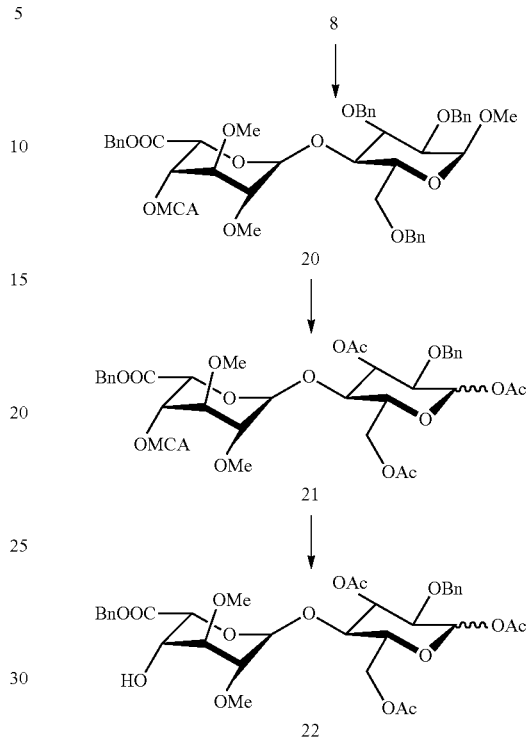

Preparation 15

Methyl 2,3,6-tri-O-benzyl-4-O-(benzyl 4-O-chloroacetyl-2,3-di-O-methyl-α-L-idopyranosyluronate)-α-D-glucopyranoside (20)

A mixture of 8 (326 mg, 0.43 mmol), of chloroacetic anhydride (103 g, 0.6 mmol), of 4-dimethylaminopyridine (5.3 mg, 42 μmol) and of triethylamine (90 μl, 64 μmol) in dichloromethane (96 ml) is stirred at ambient temperature for 30 minutes. Methanol (0.5 ml) is then added, and the solution is diluted with dichloromethane, washed with water, dried (sodium sulphate) and concentrated. Column chromatography (2:3 then 1:2 cyclohexane/ether) gives pure 20 (242 mg, 67%). TLC, $R_F$ 0.35, 1:2 cyclohexane/ether. $^1$H NMR (CDCl$_3$) δ 7.36-7.19 (m, 20H, 4Ph), 5.20 (d, 1H, H-1'), 4.56 (d, 1H, H-1), 3.70 and 3.36 (AB system, J=15.3 Hz, ClCH$_2$(C:O)O), 3.49, 3.35; 3.26 (3s, 3 OCH).

Preparation 16

1,3,6-tri-O-Acetyl-2-O-benzyl-4-O-(benzyl 4-O-chloroacetyl-2,3-di-O-methyl-α-L-idopyranosyluronate)-α,β-D-glucopyranose (21)

A solution of trifluoroacetic acid (183 μl, 2.4 mmol) is added to a solution of 20 (50 mg, 0.06 mmol) in acetic anhydride (1.28 ml, 13.5 mmol) and acetic acid (52 μl, 0.9 mol). After heating at 60° C. for 4 hours, the solution is cooled to 0° C. and neutralized with triethylamine. After evaporation, column chromatography of the residue (1:2 then 2:5 cyclohexane/ether) gives a mixture (α/β=8/2) of the anomers of 21 (28 mg, 60%). TLC, $R_F$ 0.31, 2:5 cyclohexane/ether. $^1$H NMR (CDCl$_3$) δ 7.20-7.35 (m, 10H, 2Ph), 6.30 (d, J=3.6 Hz, H-1α), 5.63 (d, J=8.1 Hz, H-1β), 3.39 and 3.46 (2s, 2 OCH$_3$).

Preparation 17

1,3,6-tri-O-Acetyl-2-O-benzyl-4-O-(benzyl 2,3-di-O-methyl-α-L-idopyranosyluronate)-α,β-D-glucopyranose (22)

Thiourea (678 mg; 8.9 mmol) is added to a solution of 21 (1.71 g; 2.23 mmol) in a mixture of pyridine (108 ml) and ethanol (22 ml), and the mixture is heated at 110° C. for 30 minutes. After cooling and evaporation, the residue is dissolved in dichloromethane. The solution is washed with the aid of a saturated aqueous solution of sodium hydrogencarbonate, then a 5% potassium hydrogensulphate solution, dried (sodium sulphate) and concentrated. Column chromatography (1:1, then 1:2 cyclohexane/ethyl acetate) gives pure 22 (1.17 g; 76%). TLC, $R_F$ 0.34; 3:1 dichloromethane/ether. $^1$H NMR (CDCl$_3$) δ 7.36-7.20 (m, 10H, 2Ph), 6.30 (d, J=3.6 Hz, H-1α), 5.65 (d, J=8 Hz, H-1β), 4.90 (1H, H-1'), 3.41 and 3.40 (2s, 2 OCH$_3$)

Preparation 18

(1-4)-O-(benzyl 4-O-Levulinyl-2,3-di-O-methyl-α-L-idopyranosyluronate)-(1-4)-O-(3,6-di-O-acetyl-2-O-benzyl-α-D-glucopyranosyl)-(1-4)-O-(benzyl 2,3-di-O-methyl-α-L-idopyranosyluronate)-1,3,6-tri-O-acetyl-2-O-benzyl-α,β-D-glucopyranose (23)

A mixture of 15 (1.5 g, 1.7 mmol) and 22 (1.18 g; 1.7 mmol) is treated according to method 3 (by replacing the toluene with dichloromethane). Gel permeation chromatography on a column of LH-20, equilibrated in dichloromethane/ethanol 1:1, gives pure 23 (1.75 g; 73%). [α]$_D$+19 (c=0.9, dichloromethane). LSIMS, positive mode: m/z thioglycerol+NaCl, 1441 (M+Na)$^+$; thioglycerol+KF, 1457 (M+K)$^+$.

$^1$H NMR (CDCl$_3$) δ: 6.27; 5.45; 5.10; 4.96; 4.90 ppm.

Anal. Calc. for C$_{71}$H$_{86}$O$_{30}$ (1419.46); C, 60.08; H, 6.11. Found: C, 60.06; H, 6.40.

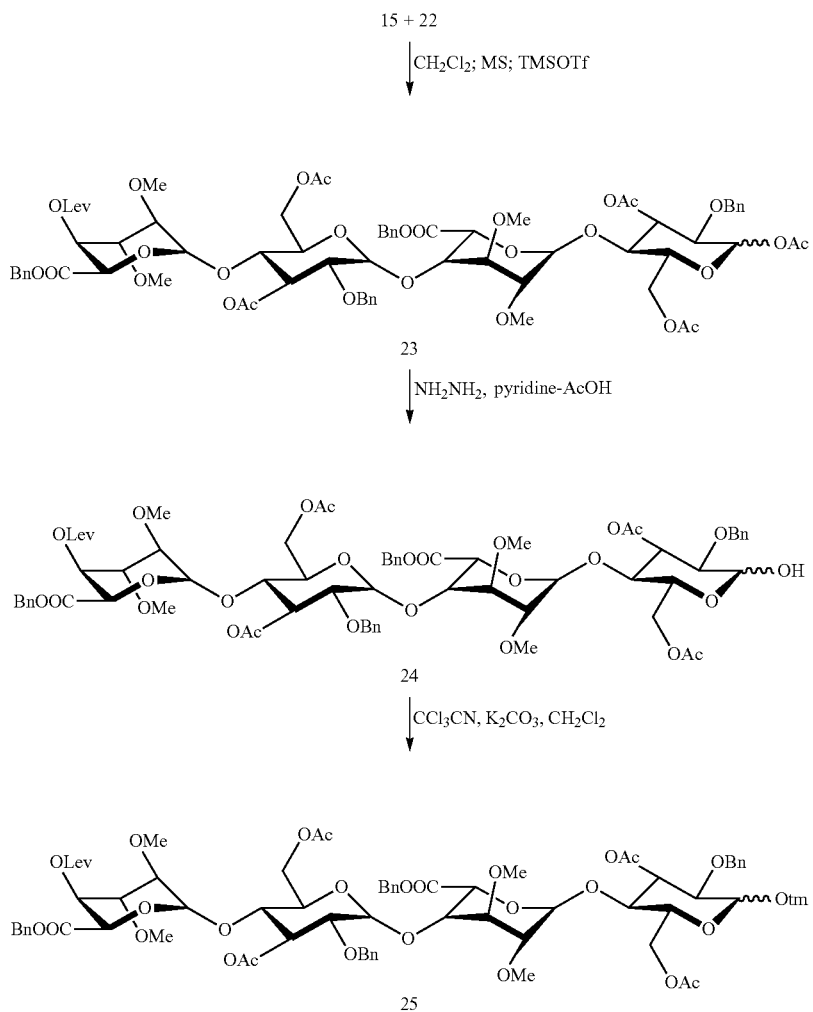

SCHEME 6
Synthesis of the tetrasaccharide imidate 25

Preparation 19

(1-4)-O-(benzyl 4-O-Levulinyl-2,3-di-O-methyl-α-L-idopyranosyluronate)-(1-4)-O-(3,6-di-O-acetyl-2-O-benzyl-α-D-glucopyranosyl)-(1-4)-O-(benzyl 2,3-di-O-methyl-α-L-idopyranosyluronate)-3,6-di-O-acetyl-2-O-benzyl-α,β-D-glucopyranose (24)

Ethanolamine (80 µl; 1.31 mmol) is added to a solution of the tetrasaccharide 23 (465 mg; 327 µmol) in tetrahydrofuran (5 ml), then the solution is left overnight at 4° C. After neutralization with hydrochloric acid (1 M; 2 ml), dichloromethane (20 ml) is added, then the solution is washed with water, dried (sodium sulphate) and concentrated. Column chromatography (3:1 toluene/acetone) gives 24 (326 mg; 79%). TLC, $R_F$ 0.33, 3:1 toluene/acetone. LSIMS, positive mode: m/z thioglycerol+NaCl, 1399 (M+Na)$^+$; thioglycerol+KF, 1415 (M+K)$^+$.

$^1$H NMR (CDCl$_3$) δ: 5.18; 5.10; 4.96; 4.93; 4.75

Preparation 20

(1-4)-O-(benzyl 4-O-Levulinyl-2,3-di-O-methyl-α-L-idopyranosyluronate)-(1-4)-O-(3,6-di-O-acetyl-2-O-benzyl-α-D-glucopyranosyl)-(1-4)-O-(benzyl 2,3-di-O-methyl-α-L-idopyranosyluronate)-3,6-di-O-acetyl-2-O-benzyl-α-α,β-D-trichloroacetimidate (25)

A mixture of trichloroacetonitrile (151 µl; 1.5 mmol), of the tetrasaccharide 24 (343 mg; 249 µM) and of potassium carbonate (62 mg; 448 µmol) in dichloromethane (2 ml) is stirred for one night at ambient temperature. Dichloromethane is added, and after filtration the solution is concentrated. Column chromatography (3:1 toluene/acetone) gives 25 (346 mg; 91%). TLC, $R_F$ 0.42; 0.63, 2:1 dichloromethane/ethyl acetate.

$^1$H NMR (CDCl$_3$) δ: 8.67 (s, NH-b), 8.59 (s, NH-a), 7.40-7.20 (m, 10H, 2Ph), 6.40 (d, J=3.5 Hz, H-1α), 5.90 (d, J=7.5 Hz, H-1β), 3.45; 3.44; 3.42; 3.40; 3.39; 3.37 (6s, 12H, 4OMe), 2.7-2.2 (m, 4H, O(C:O)CH$_2$CH$_2$(C:O)CH$_3$), 2.12; 2.08; 2.07; 2.04; 2.02; 1.91; 1.89 (7s, 15H, 4 Ac, and O(C:O)CH$_2$CH$_2$(C:O)CH$_3$). NH-a and NH-b designate the signals obtained for each of the syn and anti isomers.

Preparation 21

Methyl (1-4)-O-(benzyl 4-O-Levulinyl-2,3-di-O-methyl-α-L-idopyranosyluronate)-[(1-4)-O-(3,6-di-O-acetyl-2-O-benzyl-α-D-glucopyranosyl)-(1-4)-O-(benzyl 2,3-di-O-methyl-α-L-idopyranosyluronate)-]$_3$-2,3,6-tri-O-benzyl-α-D-glucopyranoside (26)

Starting from 17 and 25. A mixture of 17 and 25 (459 mg, 0.3 mmol) is treated according to Method 3. Column chromatography (Sephadex® LH 20, 195×3.7 cm; 1:1 dichloromethane/ethanol), followed by silica gel column chromatography (3:2 cyclohexane-acetone) gives pure 26 (420 mg; 59%). [α]$_D$+20 (c=0.20, dichloromethane). LSIMS, positive mode: m/z thioglycerol+NaCl, 2771 (M+Na)$^+$; thioglycerol+KF, 2787 (M+K)$^+$.

$^1$H NMR (CDCl$_3$) δ: 5.26; 5.14; 5.10; 4.93; 4.92; 4.90; 4.56

Preparation 22

26 starting from 15 and 19. A mixture of 15 (332 mg; 373 µmol) and 19 (377 mg; 186 µmol) is treated according to method 2. Column chromatography (Sephadex® LH 20, 195×3.7 cm; 1:1 dichloromethane/ethanol) gives the pure octasaccharide 26 (460 mg; 90%).

Preparation 23

Methyl (1-4)-O-(benzyl 2,3-di-O-Methyl-α-L-idopyranosyluronate)-[(1-4)-O-(3,6-di-O-acetyl-2-O-benzyl-α-D-glucopyranosyl)-(1-4)-O-(2,3-di-O-methyl-α-L-benzyl idopyranosyluronate)]$_3$-2,3,6-tri-O-benzyl-α-D-glucopyranoside (27)

Compound 26 (275 mg; 100 µmol) is treated according to method 1 to give 27 (265 mg; 96%); [α]$_D$+27 (c=0.56, dichloromethane). LSIMS, positive mode: m/z thioglycerol+NaCl, 2673 (M+Na)$^+$; thioglycerol+KF, 2689 (M+K)$^+$.

$^1$H NMR (CDCl$_3$) δ: 5.26; 5.15; 5.10; 5.08; 4.89; 4.88; 4.55

Preparation 24

Methyl (1-4)-O-(benzyl 4-O-levulinyl-2,3-di-O-methyl-α-L-idopyranosyluronate)-[(1-4)-O-(3,6-di-O-acetyl-2-O-benzyl-α-D-glucopyranosyl)-(1-4)-O-(benzyl 2,3-di-O-methyl-α-L-idopyranosyluronate)]$_5$-2,3,6-tri-O-benzyl-α-D-glucopyranoside (28)

A mixture of 27 (97.3 mg; 36 µmol) and of 25 (83.8 mg, 55 µmol) is treated according to method 3. Column chromatography (cyclohexane-acetone 2:1, then 7:4, then 3:2) gives pure 28 (102 mg; 69%). [α]$_D$+22 (c=0.51, dichloromethane). TLC, $R_F$ 0.18, 3:2 cyclohexane-acetone.

$^1$H NMR (CDCl$_3$) δ: 5.26; 5.14; 5.10; 5.08; 4.93; 4.92; 4.90; 4.56

Preparation 25

Methyl (1-4)-O-(benzyl 2,3-di-O-methyl-α-L-idopyranosyluronate)-[(1-4)-O-(3,6-di-O-acetyl-2-O-benzyl-α-D-glucopyranosyl)-(1-4)-O-(benzyl 2,3-di-O-methyl-α-L-idopyranosyluronate)]$_5$-2,3,6-tri-O-benzyl-α-D-glucopyranoside (29)

The compound 28 (216 mg; 54 µmol) is treated according to method 1 to give 29 (199 mg; 95%). TLC, $R_F$ 0.56, 1:1 cyclohexane-acetone; $R_F$ 0.55, 2:1 toluene-acetone. LSIMS, positive mode: m/z thioglycerol+NaCl, 3934 (M+Na)$^+$; thioglycerol+KF, 3950 (M+K)$^+$.

Preparation 26

Methyl (1-4)-O-(benzyl 4-O-levulinyl-2,3-di-O-methyl-α-L-idopyranosyluronate)-[(1-4)-O-(3,6-di-O-acetyl-2-O-benzyl-α-D-glucopyranosyl)-(1-4)-O-(benzyl 2,3-di-O-methyl-α-L-idopyranosyluronate)]$_7$-2,3,6-tri-O-benzyl-α-D-glucopyranoside (30)

A mixture of 25 (33 mg, 21.4 µmol) and of 29 (52.4 mg; 13.3 µmol) is treated according to method 2. Column chromatography (7:4 cyclohexane-acetone) gives pure 30 (43.8 mg; 62%). [α]$_D$+19 (c=0.5, dichloromethane). TLC, $R_F$ 0.36, 3:2 cyclohexane-acetone. LSIMS, positive mode: m/z thioglycerol+KF, 5310 (M+K)$^+$.

$^1$H NMR (CDCl$_3$) δ of the principal anomeric protons: 5.26; 5.14; 5.10; 5.08; 4.92; 4.90; 4.56

Preparation 27

Methyl (1-4)-O-(benzyl 2,3-di-O-methyl-α-L-idopyranosyluronate)-[(1-4)-O-(3,6-di-O-acetyl-2-O-benzyl-α-glucopyranosyl)-(1-4)-O-(benzyl 2,3-di-O-methyl-α-L-idopyranosyluronate)-]$_7$-2,3,6-tri-O-benzyl-α-D-glucopyranoside (31)

The hexadecasaccharide 30 (100 mg; 19 µmol) is treated according to method 1 to give 31 which is used directly in the following step. [α]$_D$+20 (c=0.38, dichloromethane). TLC, R$_F$ 0.31, 4:3 cyclohexane-acetone. LSIMS, positive mode: m/z thioglycerol+NaCl, 5196 (M+Na)$^+$; thioglycerol+KF, 5212 (M+K)$^+$.

Preparation 28

Methyl (1-4)-O-(benzyl 4-O-levulinyl-2,3-di-O-methyl-α-L-idopyranosyluronate)-[(1-4)-O-(3,6-di-O-acetyl-2-O-benzyl-α-D-glucopyranosyl)-(1-4)-O-(benzyl 2,3-di-O-methyl-α-L-idopyranosyluronate)]$_9$- 2,3,6-tri-O-benzyl-α-D-glucopyranoside (32)

A mixture of 25 (31 mg; 21.7 µmol) and of 31 (94.5 mg, 18.3 µmol) is treated according to method 3 to give 32 after several column chromatography steps (29.2 mg; 25%). [α]$_D$+ 22 (c=0.33, dichloromethane). TLC, R$_F$ 0.26; 4:3 cyclohexane-acetone.

$^1$H NMR (CDCl$_3$) δ of the principal anomeric protons: 5.26; 5.14; 5.10; 5.09; 4.92; 4.91; 4.90; 4.56 ppm.

EXAMPLE 1

Methyl (1-4)-O-(2,3-di-O-methyl-4-O-sulpho-α-L-idopyranosyluronic acid)-[(1-4)-O-(2,3,6-tri-O-sulpho-α-D-glucopyranosyl)-(1-4)-O-(2,3-di-O-methyl-α-L-idopyranosyluronic acid)]$_9$-2,3,6-tri-O-sulpho-α-D-glucopyranoside, sodium salt (33)

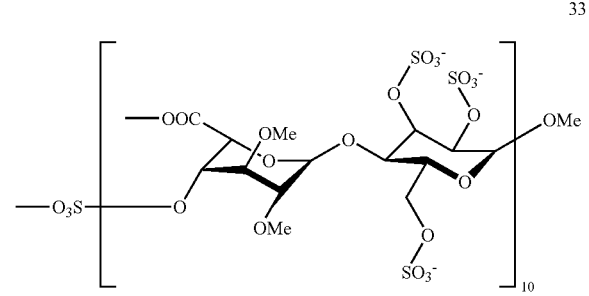

Compound 32 is treated according to method 4 to give 33 (60% over the three steps). [α]$_D$+27 (c=0.4, D$_2$O); ESIMS, negative mode: experimental mass=7077.3 α 3.2 a.m.u.

$^1$H NMR (D$_2$O) δ principal anomeric protons: δ 5.41; 5.40; 5.15; 5.09; 5.07; 5.06 ppm.

Proceeding according to EXAMPLE 1 and according to SCHEME 1 above, compounds 34 to 38 (EXAMPLES 2 to 6) described in TABLE I below are prepared.

TABLE I (I.1)

| Example number | m | [α]$_D$ | Experimental mass |
|---|---|---|---|
| 2 Compound 34 | 5 | +30 | 3605 |
| 3 Compound 35 | 6 | +29 | 4297 |
| 4 Compound 36 | 7 | +27 | 4993 |
| 5 Compound 37 | 8 | +34 | 5688 |
| 6 Compound 38 | 9 | +27 | 6381 |

EXAMPLE 7

Methyl (1-4)-O-(2,3-di-O-methyl-4-O-sulpho-β-D-glucopyranosyluronic acid)-[(1-4)-O-(2,3,6-tri-O-sulpho-α-D-glucopyranosyl)-(1-4)-O-(2,3-di-O-methyl-β-D-glucopyranosyluronic acid)]$_4$-2,3,6-tri-O-sulpho-α-D-glucopyranoside, sodium salt (39)

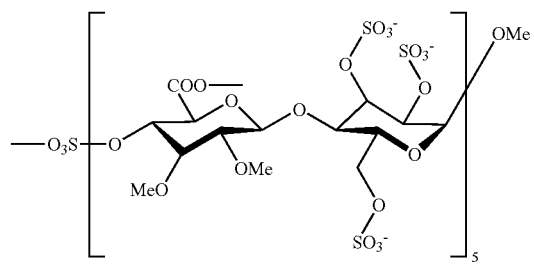

The glycosyl donor disaccharide

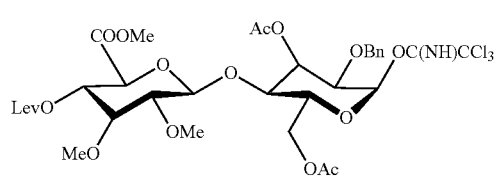

and the glycosyl acceptor disaccharide

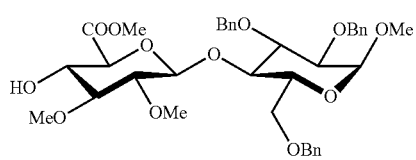

are prepared according to the methods described in Westerduin et al., BioOrg. Med. Chem., 2, 1994, 1267, then combined as described during the preparation of 34. The resultant decasaccharide is treated according to method 4 to give 39.

$[\alpha]_D$+45 (c=1, $H_2O$). $^1H$ NMR ($D_2O$) δ of the principal anomeric protons: 5.53; 5.18; 4.65; 4.63 ppm.

Proceeding according to EXAMPLE 7 and according to SCHEME 1 above, compound 40 (EXAMPLE 8) described in TABLE II below is prepared.

TABLE II (I.1)

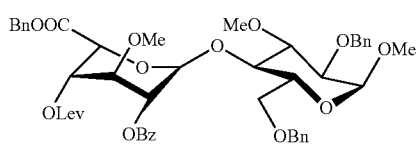

| Example number | m | $[\alpha]_D$ | $^1H$ NMR ($D_2O$) δ(ppm) of the principal anomeric protons |
|---|---|---|---|
| 8 Compound 40 | 4 | +45 | 5.53; 5.13; 4.62; 4.60 |

Example 9

Methyl (1-4)-O-(3-O-methyl-2,4-di-O-sulpho-α-L-idopyranosyluronic acid)-[(1-4)-O-(3-O-methyl-2,6-di-O-sulpho-α-D-glucopyranosyl)-(1-4)-O-(3-O-methyl-2-O-sulpho-α-L-idopyranosyluronic acid)]$_4$-3-O-methyl-2,6-di-O-sulpho-α-D-glucopyranoside, sodium salt (41)

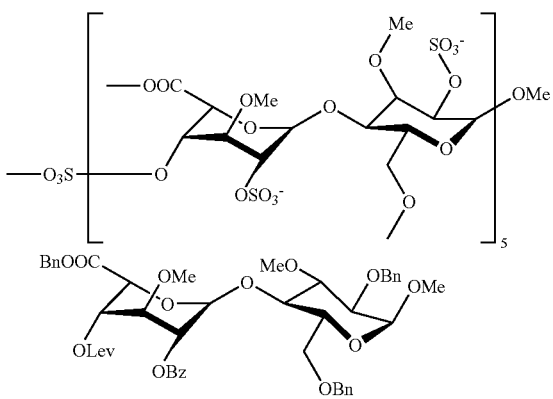

The disaccharide synthon (TLC, $R_F$ 0.54, 1:1 cyclohexane/EtOAc) is treated as described for 12 to give the glycosyl donor imidate

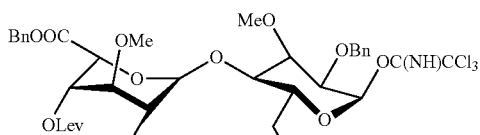

and the acceptor

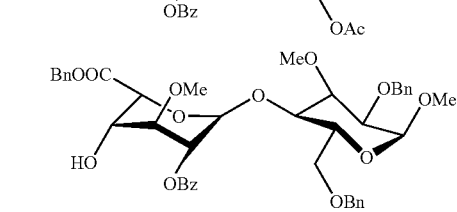

[$^1H$ NMR (CDCl$_3$) δ 8.00-7.15 (m, 20H, 4Ph), 5.15 (d, 1H, H-1'), 4.57 (d, 1H, H-1), 3.48; 3.47; 3.32 (3s, 3 (OCH$_3$)].

These three synthons are then combined as is described for the preparation of 34. The resultant decasaccharide is then treated according to the method 4 to give 41.

$[\alpha]_D$+17 (c=1, $H_2O$). $^1H$ NMR ($D_2O$) δ of the principal anomeric protons: 5.36; 5.34; 5.13; 5.11; 5.09; 5.05 ppm.

Proceeding according to EXAMPLE 9 and according to SCHEME 1 above, the compounds 42 and 43 (EXAMPLE 10 and 11) described in TABLE III below are prepared.

TABLE III (I.2)

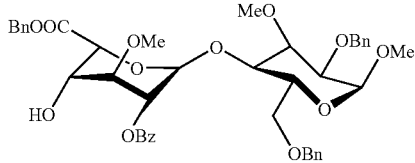

| Example number | m | $^1H$ NMR ($D_2O$ δ (ppm) [600 MHz] of the principal anomeric protons |
|---|---|---|
| 10 Compound 42 | 4 | 5.20; 5.17; 5.12; 5.03; 4.90 |
| 11 Compound 43 | 6 | 5.20; 4.99; 4.95; 4.90 |

EXAMPLE 12

Methyl (1-4)-O-(3-O-methyl-2,4-di-O-sulpho-β-D-glucopyranosyluronic acid)-[(1-4)-O-(3-O-methyl-2,6-di-O-sulpho-α-D-glucopyranosyl)-(1-4)-O-(3-O-methyl-2-O-sulpha-β-D-glucopyranosyluronic acid)]₄-3-O-methyl-2,6-di-O-sulpho-α-D-glucopyranoside, sodium salt (44)

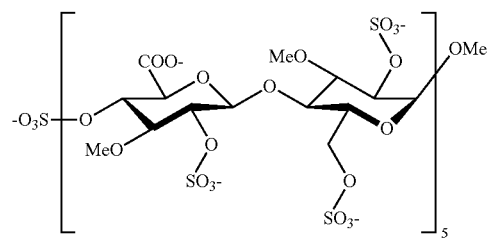

The disaccharide synthons

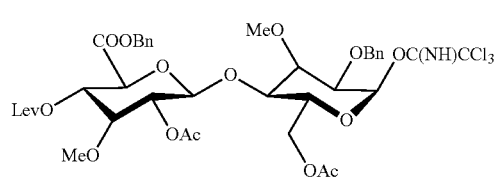

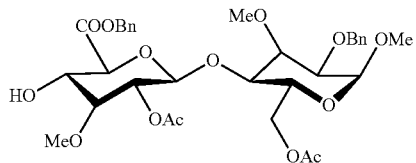

are prepared and then combined as described for 34. The decasaccharide obtained treated according to method 4 gives 44:

[α]_D +25 (c=0.2, H₂O). ¹H NMR (D₂O) δ of the principal anomeric protons: 5.47; 5.07; 4.74; 4.71; 4.70 ppm.

EXAMPLE 13

Methyl (1-4)-O-(3-O-methyl-2,4-di-O-sulpho-α-L-idopyranosyluronic acid)-[(1-4)-O-(—O-methyl-2,6-di-O-sulpho-α-D-glucopyranosyl)-(1-4)-O-(3-O-methyl-2-O-sulpho-α-L-idopyranosyluronic acid)]₂-(1-4)-O-(2,3,6-tri-O-sulpho-α-D-glucopyranosyl)-(1-4)-O-(3-O-methyl-2-O-sulpho-α-L-idopyranosyluronic acid)-3-O-methyl-2,6-di-O-sulpho-α-D-glucopyranoside, sodium salt (45)

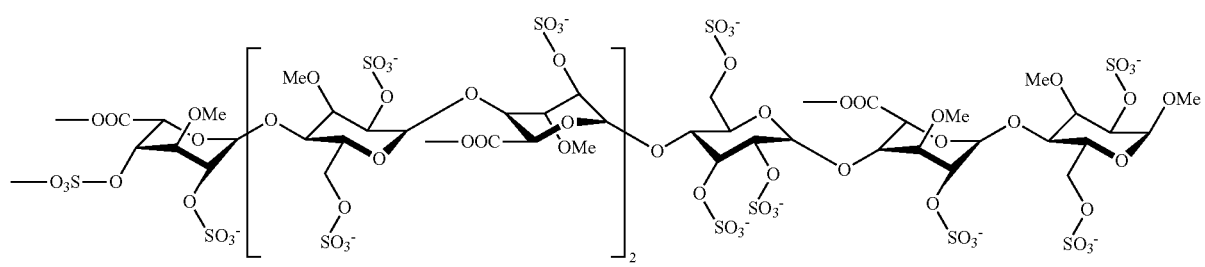

The glycosyl donor 15 and the glycosyl acceptor

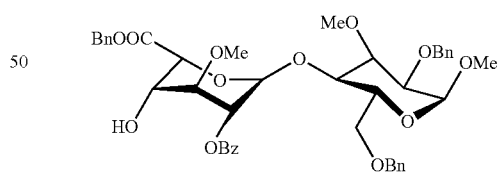

combined according to method 3 give the tetrasaccharide

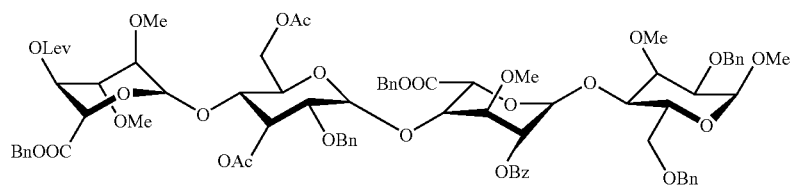

After cleavage of the Lev group (method 1) and repeated reaction with the following glycosyl donor disaccharide, according to the principle described in Scheme 1,

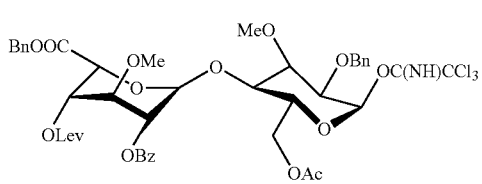

5 the completely protected precursor of 45 is obtained, which is treated according to method 4 to give 45.

$^1$H NMR (D$_2$O) δ (ppm) [600 MHz] of the principal anomeric protons: 5.35; 5.33; 5.30; 5.22; 5.21; 5.18; 5.15; 4.98.

Proceeding to EXAMPLE 13 and according to SCHEME 1 above starting from completely protected oligosaccharide precursors, compound 46 (EXAMPLE 14) described in TABLE IV below is prepared.

-continued

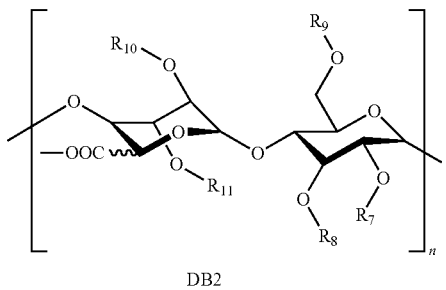

DB2

TABLE IV (I.3)

| Example number | m | $^1$H NMR (D$_2$O) δ (ppm) [600 MHz] of the principal anomeric protons |
|---|---|---|
| 14 Compound 46 | 3 | 5.34; 5.32; 5.27; 5.22; 5.14; 4.98 |

The invention claimed is:

1. A synthetic polysaccharide containing from 8 to 24 monosaccharide units comprising a sequence of disaccharides formed from a uronic acid and from a hexose, said polysaccharide having its hydroxyl groups etherified with a (C$_1$-C$_6$)alkyl group or esterified in the form of a sulpho group, each disaccharide being at least monoetherified, having the formula:

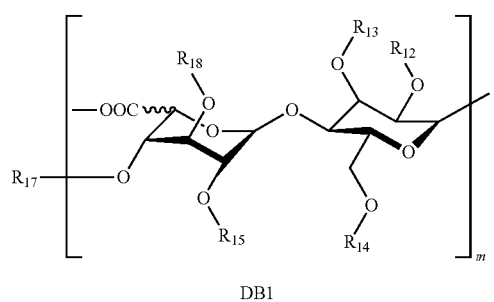

DB1

(I)

-continued

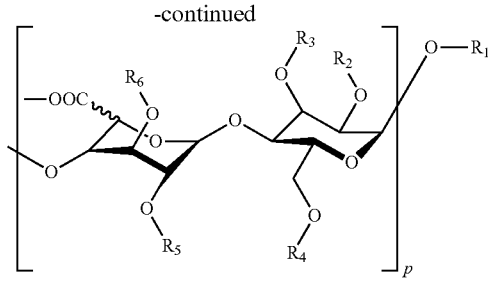

DB3 in which
the wavy line indicates either a bond below or above the plane of the pyranose ring;
R$_1$, R$_6$, R$_{11}$ and R$_{16}$ are a (C$_1$-C$_6$)alkyl;
R$_2$, R$_3$, R$_4$, R$_5$, R$_7$, R$_8$, R$_9$, R$_{10}$, R$_{12}$, R$_{13}$, R$_{14}$, R$_{15}$ and R$_{17}$ are a (C$_1$-C$_6$)alkyl or an SO$_3^-$ group;
m, n and p are such that the sum m+n+p is greater than or equal to 4 and less than or equal to 12, one or two of the three being able to be zero;
and the salts thereof and the acids corresponding thereto.

2. A polysaccharide according to claim 1 formed from an anion and from a cation, wherein the anion has the formula (I.1):

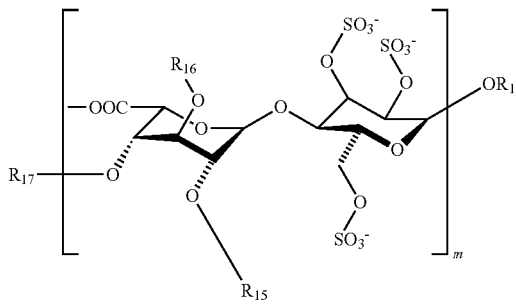

(I.1)

in which m is 4 to 10; $R_1$ and $R_{16}$ are a ($C_1$-$C_6$)alkyl and $R_{15}$ and $R_{17}$ are a ($C_1$-$C_6$)alkyl or an $SO_3^-$ group, each uronic acid being either an iduronic or glucuronic acid; and the cation is a pharmaceutically acceptable monovalent cation; and the salts thereof and the acids corresponding thereto.

3. A polysaccharide of claim 1 wherein the alkyls are methyls and the salts thereof and the acids corresponding thereto.

4. A polysaccharide of claim 1 wherein n and p are equal to zero and the salts thereof and the acids corresponding thereto.

5. A polysaccharide of claim 1 wherein n and p are equal to zero and m is 4 to 10 and the salts thereof and the acids corresponding thereto.

6. A polysaccharide of claim 1 wherein n and p are equal to zero, m is 4 to 10; at least one of the substituents $R_{12}$, $R_{13}$, $R_{14}$ and $R_{15}$ is a sulphate group; $R_1$ and $R_{16}$ are a ($C_1$-$C_6$)alkyl and $R_{17}$ is a ($C_1$-$C_6$)alkyl or an $SO_3^-$ group and the salts thereof and the acids corresponding thereto.

7. A polysaccharide of claim 1 wherein n and p are equal to zero, m is 4 to 10; at least two of the substituents $R_{12}$, $R_{13}$, $R_{14}$ and $R_{15}$ are a sulphate group; $R_1$ and $R_{16}$ are a ($C_1$-$C_6$)alkyl and $R_{17}$ is a ($C_1$-$C_6$)alkyl or an $SO_3^-$ group and the salts thereof and the acids corresponding thereto.

8. A polysaccharide of claim 1 wherein n and p are equal to zero, m is 4 to 10; at least three of the substituents $R_{12}$, $R_{13}$, $R_{14}$ and $R_{15}$ are a sulphate group; $R_1$ and $R_{16}$ are a ($C_1$-$C_6$)alkyl and $R_{17}$ is a ($C_1$-$C_6$)alkyl or an $SO_3^-$ group and the salts thereof and the acids corresponding thereto.

9. A polysaccharide according to claim 2 in which the cation is selected from sodium and potassium.

10. A polysaccharide according to claim 1 formed from an anion and from a cation, wherein the anion has the formula (I.2):

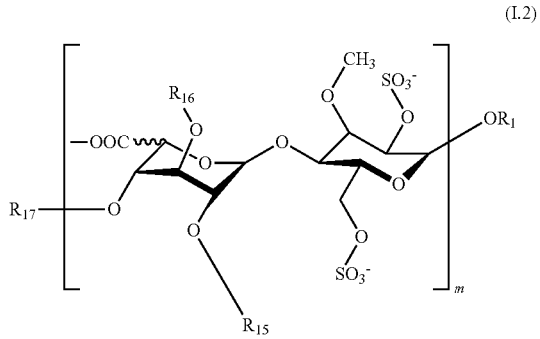

(I.2)

in which m is 4 to 10; $R_1$ and $R_{16}$ are a ($C_1$-$C_6$)alkyl and $R_{15}$ and $R_{17}$ are a ($C_1$-$C_6$)alkyl or an $SO_3^-$ group, each uronic acid being either an iduronic or glucuronic acid; and the cation is a pharmaceutically acceptable monovalent cation; and the salts thereof and the acids corresponding thereto.

11. A polysaccharide according to claim 1 formed from an anion and from a cation, wherein the anion has the formula (I.3):

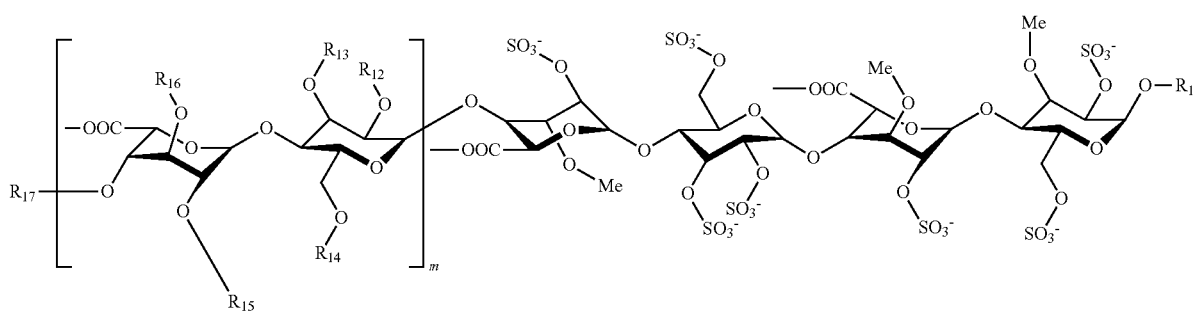

(I.3)

in which m is 2 or 3; $R_1$ and $R_{16}$ are a $(C_1$-$C_6)$alkyl and $R_{12}$, $R_{13}$, $R_{14}$, $R_{15}$ and $R_{17}$ are a $(C_1$-$C_6)$alkyl or an $SO_3^-$ group, each uronic acid being either an iduronic or glucuronic acid; and the cation is a pharmaceutically acceptable monovalent cation; as well as the salts thereof and the acids corresponding thereto.

12. A polysaccharide according to claim 11 in which $R_1$ is a methyl, $R_{13}$ in position 3 of the glucose is a methyl, $R_{12}$ in position 2 and $R_{14}$ in position 6 of the glucose are an $SO_3^-$ and $R_{16}$ in position 3 of the iduronic or glucuronic unit is a methyl, and m is equal to 2 or 3.

13. A polysaccharide chosen from the group consisting of:
methyl (1-4)-O-(2,3-di-O-methyl-4-O-sulpho-α-L-idopyranosyluronic acid)-[(1-4)-O-(2,3,6-tri-O-sulpho-α-D-glucopyranosyl)-(1-4)-O-(2,3-di-O-methyl-α-L-idopyranosyluronic acid)]$_9$-2,3,6-tri-O-sulpho-α-D-glucopyranoside, sodium salt, methyl (1-4)-O-(2,3-di-O-methyl-4-O-sulpho-α-L-idopyranosyluronic acid)-[(1-4)-O-(2,3,6-tri-O-sulpho-α-D-glucopyranosyl)-(1-4)-O-(2,3-di-O-methyl-α-L-idopyranosyluronic acid)]$_4$-2,3,6-tri-O-sulpho-α-D-glucopyranoside, sodium salt, methyl (1-4)-O-(2,3-di-O-methyl-4-O-sulpho-α-L-idopyranosyluronic acid)-[(1-4)-O-(2,3,6-tri-O-sulpho-α-D-glucopyranosyl)-(1-4)-O-(2,3-di-O-methyl-α-L-idopyranosyluronic acid)]$_5$-2,3,6-tri-O-sulpho-α-D-glucopyranoside, sodium salt, methyl (1-4)-O-(2,3-di-O-methyl-4-O-sulpho-α-L-idopyranosyluronic acid)-[(1-4)-O-(2,3,6-tri-O-sulpho-α-D-glucopyranosyl)-(1-4)-O-(2,3-di-O-methyl-α-L-idopyranosyluronic acid)]$_6$-2,3,6-tri-O-sulpho-α-D-glucopyranoside, sodium salt, methyl (1-4)-O-(2,3-di-O-methyl-4-O-sulpho-α-L-idopyranosyluronic acid)-[(1-4)-O-(2,3,6-tri-O-sulpho-α-D-glucopyranosyl)-(1-4)-O-(2,3-di-O-methyl-α-L-idopyranosyluronic acid)]$_7$-2,3,6-tri-O-sulpho-α-D-glucopyranoside, sodium salt, methyl (1-4)-O-(2,3-di-O-methyl-4-O-sulpho-α-L-idopyranosyluronic acid)-[(1-4)-O-(2,3,6-tri-O-sulpho-α-D-glucopyranosyl)-(1-4)-O-(2,3-di-O-methyl-α-L-idopyranosyluronic acid)]$_8$-2,3,6-tri-O-sulpho-α-D-glucopyranoside, sodium salt, methyl (1-4)-O-(2,3-di-O-methyl-4-O-sulpho-β-D-glucopyranosyluronic acid)-[(1-4)-O-(2,3,6-tri-O-sulpho-α-D-glucopyranosyl)-(1-4)-O-(2,3-di-O-methyl-β-D-glucopyranosyluronic acid)]$_4$-2,3,6-tri-O-sulpho-α-D-glucopyranoside, sodium salt, methyl (1-4)-O-(2,3-di-O-methyl-4-O-sulpho-β-D-glucopyranosyluronic acid)-[(1-4)-O-(2,3,6-tri-O-sulpho-α-D-glucopyranosyl)-(1-4)-O-(2,3-di-O-methyl-β-D-glucopyranosyluronic acid)]$_3$-2,3,6-tri-O-sulpho-α-D-glucopyranoside, sodium salt, methyl (1-4)-O-(3-O-methyl-2,4-di-O-sulpho-α-L-idopyranosyluronic acid)-[(1-4)-O-(3-O-methyl-2,6-di-O-sulpho-α-D-glucopyranosyl)-(1-4)-O-(3-O-methyl-2-O-sulpho-α-L-idopyranosyluronic acid)]$_4$-3-O-methyl-2,6-di-O-sulpho-α-D-glucopyranoside, sodium salt, methyl (1-4)-O-(3-O-methyl-2,4-di-O-sulpho-α-L-idopyranosyluronic acid)-[(1-4)-O-(3-O-methyl-2,6-di-O-sulpho-α-D-glucopyranosyl)-(1-4)-O-(3-O-methyl-2-O-sulpho-α-L-idopyranosyluronic acid)]$_3$-3-O-methyl-2,6-di-O-sulpho-α-D-glucopyranoside, sodium salt, methyl O-(3-O-methyl-2,4-di-O-sulpho-α-L-idopyranosyluronic acid)-[(1-4)-O-(3-O-methyl-2,6-di-O-sulpho-α-D-glucopyranosyl)-(1-4)-O-(3-O-methyl-2-O-sulpho-α-L-idopyranosyluronic acid)(1-4)-]$_5$-3-O-methyl-2,6-di-O-sulpho-α-D-glucopyranoside, sodium salt, methyl (1-4)-O-(3-O-methyl-2,4-di-O-sulpho-β-D-glucopyranosyluronic acid)-[(1-4)-O-(3-O-methyl-2,6-di-O-sulpho-α-D-glucopyranosyl)-(1-4)-O-(3-O-methyl-2-O-sulpho-β-D-glucopyranosyluronic acid)]$_4$-3-O-methyl-2,6-di-O-sulpho-α-D-glucopyranoside, sodium salt, methyl (1-4)-O-(3-O-methyl-2,4-di-O-sulpho-α-L-idopyranosyluronic acid)-[(1-4)-O-(3-O-methyl-2,6-di-O-sulpho-α-D-glucopyranosyl)-(1-4)-O-(3-O-methyl-2-O-sulpho-α-L-idopyranosyluronic acid)]$_2$-O-(2,3,6-tri-O-sulpho-α-D-glucopyranosyl)-(1-4)-O-(3-(1-4)-O-methyl-2-O-sulpho-α-L-idopyranosyluronic acid)-3-O-methyl-2,6-di-O-sulpho-α-D-glucopyranoside, sodium salt, and methyl (1-4)-O-(3-O-methyl-2,4-di-O-sulpho-α-L-idopyranosyluronic acid)-[(1-4)-O-(3-O-methyl-2,6-di-O-sulpho-α-D-glucopyranosyl)-(1-4)-O-(3-O-methyl-2-O-sulpho-α-L-idopyranosyluronic acid)]$_3$-(1-4)-O-(2,3,6-tri-O-sulpho-α-D-glucopyranosyl)-(1-4)-O-(3-O-methyl-2-O-sulpho-α-L-idopyranosyluronic acid)-3-O-methyl-2,6-di-O-sulpho-α-D-glucopyranoside, sodium salt.

14. A process for the preparation of compounds of formula (I):

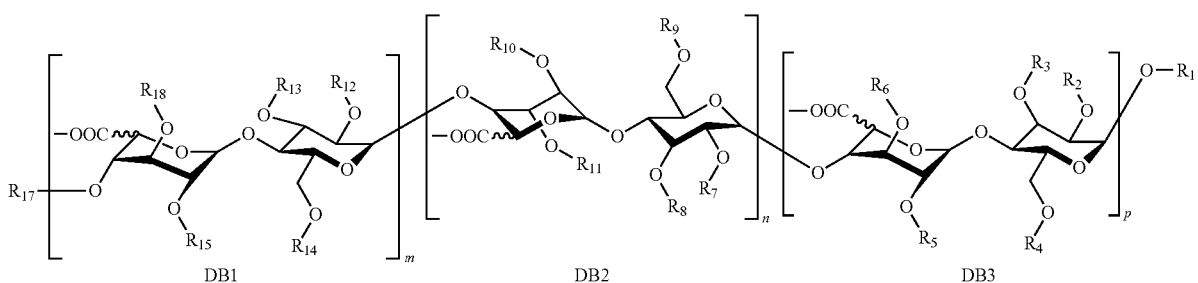

and the salts
in which
the wavy line indicates either a bond below or above the plane of the pyranose ring;
$R_1$, $R_6$, $R_{11}$ and $R_{16}$ are a $(C_1$-$C_6)$alkyl;
$R_2$, $R_3$, $R_4$, $R_5$, $R_7$, $R_8$, $R_9$, $R_{10}$, $R_{12}$, $R_{13}$, $R_{14}$, $R_{15}$ and $R_{17}$ are a $(C_1$-$C_6)$alkyl or an $SO_3^-$ group;
m, n and p are such that the sum m+n+p is greater than or equal to 4 and less than or equal to 12, one or two of the three being able to be zero;
said process comprising the steps of:
(a) coupling a glycosidic link donor monosaccharide to a glycosidic link acceptor monosaccharide to obtain an intermediate saccharide synthon of completely protected disaccharide type of formula (A):

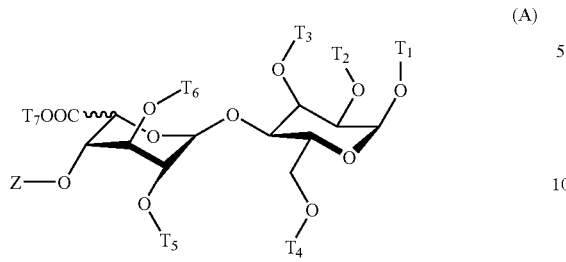
(A)

in which the identical or different $T_1$, $T_2$, $T_3$, $T_4$, $T_5$, $T_6$, $T_7$ and Z substituents are selected from the protective groups used in sugar chemistry as permanent, semi-permanent or temporary protective groups, (b) chemically modifying the disaccharide of formula (A) above to obtain an intermediate saccharide synthon of glycosidic link donor disaccharide type of formula (B):

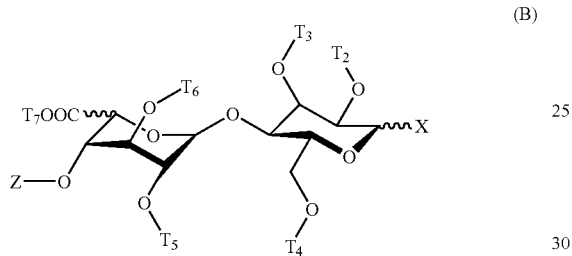
(B)

in which $T_2$ to $T_7$ and Z are as defined above for (A) and X is an activating group of the anomeric carbon, then (c) chemically modifying the disaccharide of formula (A) above to obtain an intermediate saccharide synthon of glycoside link acceptor disaccharide type of formula (C):

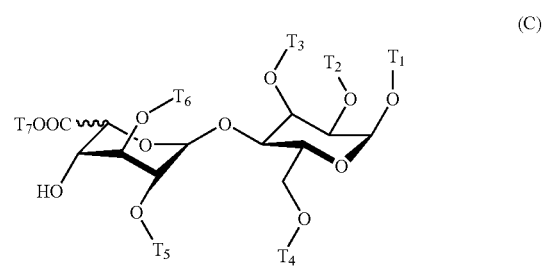
(C)

in which $T_1$ to $T_7$ are such as defined above for (A), by selectively eliminating the protective group Z, then (d) coupling a glycosidic link donor disaccharide of formula (B) obtained above and a glycosidic link acceptor disaccharide of formula (C) obtained above to obtain a completely protected tetrasaccharide of formula (D):

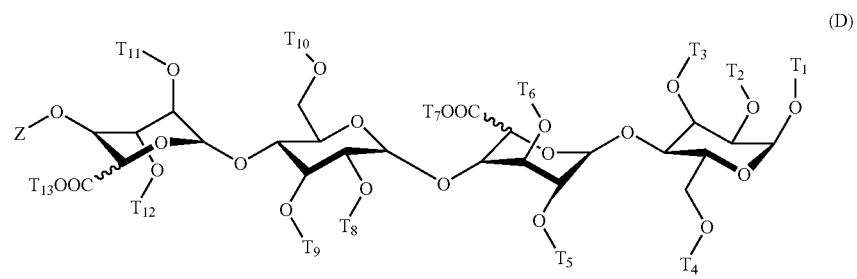
(D)

in which $T_1$ to $T_7$ and Z are such as defined above for (A) and $T_8$, $T_9$, $T_{10}$, $T_{11}$, $T_{12}$ and $T_{13}$ are such as defined for $T_2$ to $T_7$ then, (e) chemically modifying the intermediate saccharide synthon of tetrasaccharide type of formula (D) to obtain an intermediate saccharide synthon of glycosidic link donor tetrasaccharide type of formula (E):

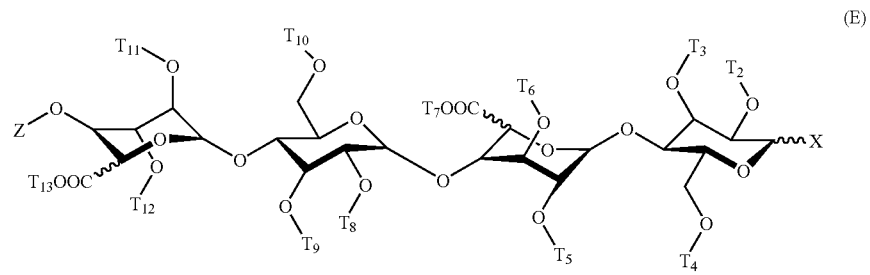
(E)

in which X has the same definition as for (B) and $T_2$ to $T_{13}$ are such as defined for (D) then, (f) selectively deprotecting the tetrasaccharide of formula (D) to obtain a glycosidic link acceptor tetrasaccharide of formula (F):

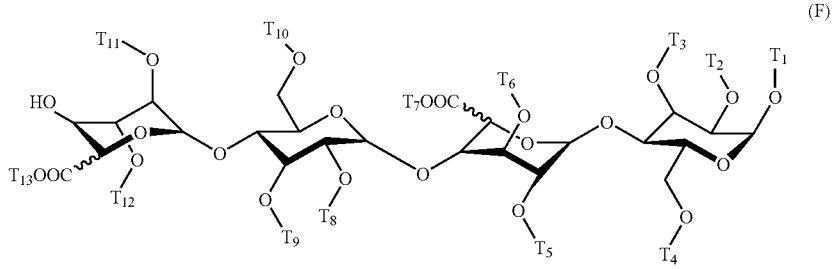

(F)

in which $T_1$ to $T_{13}$ are such as defined above for (D) then,
(g) coupling the glycosidic link acceptor tetrasaccharide of formula (F) and a glycosidic link donor disaccharide of formula (B) such as those obtained above to form an intermediate synthon of completely protected hexasaccharide type of formula (G):

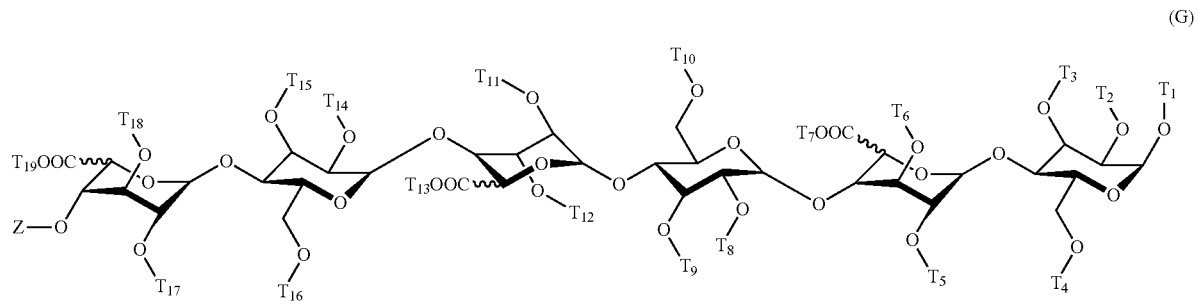

(G)

in which $T_1$ to $T_{13}$ are such as defined above for (D) and $T_{14}$ to $T_{19}$ are such as defined for $T_2$ to $T_7$ for (B);
or coupling the glycosidic link acceptor tetrasaccharide of formula (F) and a glycosidic link donor tetrasaccharide of formula (E) to obtain a completely protected octasaccharide of formula (H):

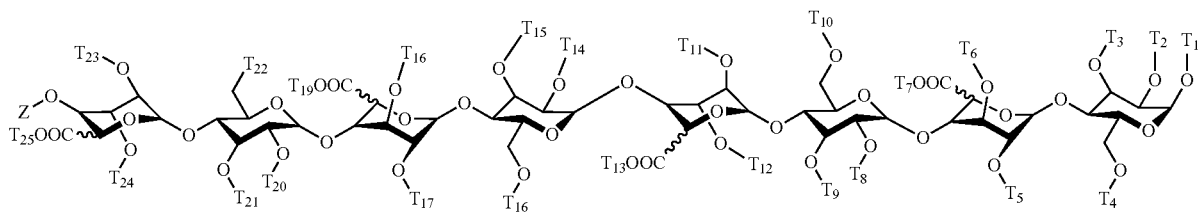

(H)

in which $T_1$ to $T_{19}$ and Z are such as defined previously and $T_{20}$ to $T_{25}$ are such as defined for $T_2$ to $T_7$ for (B) then, (h) chemically modifying the hexasaccharide of formula (G) or the octasaccharide of formula (H) obtained above to obtain an intermediate synthon of glycosidic link acceptor hexasaccharide type of formula (G) in which Z is hydrogen or else a glycosidic link acceptor octasaccharide of formula (H) in which Z is hydrogen, (i) repeating the above deprotection and coupling steps until the completely protected oligosaccharide having the desired structure is obtained, the glycosyl donor and glycosyl acceptor intermediate saccharide synthons being chosen as a function of the final structure to thus obtain the protected precursor of the desired final polysaccharide of formula (I), in which the nature of the protective substituents determines the position of the alkyl and sulphate groups on the final product (I), and (j) deprotecting the alcohol functions which must be sulphated by eliminating the substituents $T_1$ to $T_{25}$ which protected the functions in the course of the steps of elaboration of the skeleton, then, finally (k) carrying out the sulphation to obtain the compounds (I), or one of their salts.

15. A pharmaceutical composition containing a polysaccharide or salt thereof according to claim 1 in-combination with an inert, non-toxic, pharmaceutically acceptable excipient.

16. A pharmaceutical composition according to claim 15, in the form of a dosage unit.

17. A pharmaceutical composition according to claim 16 in which each dosage unit contains from 0.1 to 100 mg of the polysaccharide.

18. A pharmaceutical composition according to claim 17 in which each dosage unit contains from 0.5 to 50 mg of the polysaccharide.

19. The polysaccharide according to claim 10 in which the cation is selected from sodium and potassium.

20. The polysaccharide according to claim 11 in which the cation is selected from sodium and potassium.

* * * * *

UNITED STATES PATENT AND TRADEMARK OFFICE
CERTIFICATE OF CORRECTION

PATENT NO.       : 7,919,614 B2
APPLICATION NO.  : 10/677894
DATED            : April 5, 2011
INVENTOR(S)      : Philippe Duchaussoy et al.

It is certified that error appears in the above-identified patent and that said Letters Patent is hereby corrected as shown below:

Title Page, Item (73) Assignee should read:

(73) Assignees: SANOFI, Paris (FR)

Signed and Sealed this
Twenty-eighth Day of May, 2013

Teresa Stanek Rea
*Acting Director of the United States Patent and Trademark Office*